US008663941B2

(12) United States Patent
Hess et al.

(10) Patent No.: US 8,663,941 B2
(45) Date of Patent: Mar. 4, 2014

(54) METHOD FOR DIAGNOSING AND MONITORING CARDIAC ISCHEMIA IN PATIENTS WITH ACUTE CHEST PAIN AND WITHOUT MYOCARDIAL INFARCTION

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/480,452

(22) Filed: May 24, 2012

(65) Prior Publication Data

US 2012/0264138 A1 Oct. 18, 2012

Related U.S. Application Data

(63) Continuation of application No. PCT/EP2010/068391, filed on Nov. 29, 2010.

(30) Foreign Application Priority Data

Nov. 27, 2009 (EP) .................................... 09177395

(51) Int. Cl.
*G01N 33/573* (2006.01)
(52) U.S. Cl.
USPC ........................................... 435/7.4; 530/380
(58) Field of Classification Search
None
See application file for complete search history.

(56) References Cited

U.S. PATENT DOCUMENTS

| 5,744,305 A | 4/1998 | Fodor et al. |
| 2007/0218498 A1 | 9/2007 | Buechler et al. |
| 2009/0042228 A1* | 2/2009 | Hess et al. ...................... 435/17 |
| 2009/0155827 A1 | 6/2009 | Zeiher et al. |

FOREIGN PATENT DOCUMENTS

| WO | 2008/074781 A1 | 6/2008 |
| WO | 2008/145689 A1 | 12/2008 |
| WO | 2009/033831 A1 | 3/2009 |

OTHER PUBLICATIONS

Anderson, Page A. W. et al., "Molecular Basis of Human Cardiac Troponin T Isoforms Expressed in the Developing, Adult, and Failing Heart," Circulation Research, 1995, pp. 681-686, vol. 76 No. 4.
Bonow, Robert O., "New Insights Into the Cardiac Natriuretic Peptides," Circulation, 1996, pp. 1946-1950, vol. 93.
Braunwald, Eugene et al., ACC/AHA Guideline Update for the Management of Patients With Unstable Angina and Non-ST-Segment Elevation Myocardial Infarction—2002: Summary Article, A Report of the American College of Cardiology/American Heart Association Task Force on Practice Guidelines (Committee on the Management of Patients With Unstable Angina), Circulation, 2002, pp. 1893-1900, vol. 106.
Cannon, Christopher P. and Lee, Thomas H., "Approach to the Patient with Chest Pain," Braunwald's Heart Disease, A Textbook of Cardiovascular Medicine by Peter Libby et al., Eighth Edition, 2007, Ch. 49, pp. 1195-1196, Saunders Elsevier.
Ferrieres, Gaelle et al., "Human cardiac troponin I: precise identification of antigenic epitopes and prediction of secondary structure," Clinical Chemistry, 1998, pp. 487-493, vol. 44, No. 3.
Hanley, James A. and McNeil, Barbara J., "The Meaning and Use of the Area under a Receiver Operating Characteristic (ROC) Curve," Radiology, Apr. 1982, pp. 29-36, vol. 143.
Levey, Andrew S. and Coresh, Josef, "K/DOQI Clinical Practice Guidelines on Chronic Kidney Disease, Part 4. Definition and Classification of Stages of Chronic Kidney Disease," American Journal of Kidney Diseases, 2002, pp. S46-S47, vol. 39, Supplement 1.
Morrow, David A. et al., "National Academy of Clinical Biochemistry Laboratory Medicine Practice Guidelines: Clinical Characteristics and Utilization of Biochemical Markers in Acute Coronary Syndromes," Circulation, 2007, pp. e356-e375, vol. 115.
Moses, Marsha A. et al., "Troponin I is present in human cartilage and inhibits angiogenesis," Proceedings of the National Academy of Sciences, Mar. 1999, pp. 2645-2650, vol. 96.
Needleman, Saul B. and Wunsch, Christian D., "A General Method Applicable to the Search for Similarities in the Amino Acid Sequence of Two Proteins," Journal of Molecular Biology, 1970, pp. 443-453, vol. 48.
Nolan, John P. and Sklar, Larry A., "Suspension array technology: evolution of the flat-array paradigm," Trends in Biotechnology, Jan. 2002, pp. 9-12, vol. 20, No. 1.
O'Donoghue, Michelle et al., "Prognostic Utility of Heart-Type Fatty Acid Binding Protein in Patients With Acute Coronary Syndromes," Circulation, 2006, pp. 550-557, vol. 114.
Okamoto, Fumio et al., "Human Heart-Type Cytoplasmic Fatty Acid-Binding Protein (H-FABP) for the Diagnosis of Acute Myocardial Infarction. Clinical Evaluation of H-FABP in Comparison with Myoglobin and Creative Kinase Isoenzyme MB," Clinical Chemistry and Laboratory Medicine, 2000, pp. 231-238, vol. 38, No. 3.
Ordway, George A. and Garry, Daniel J., "Myoglobin: an essential hemoprotein in striated muscle," The Journal of Experimental Biology, 2004, pp. 3441-3446, vol. 207.
Pearson, William R. and Lipman, David J., "Improved tools for biological sequence comparison," Proceedings of the National Academy of Sciences, Apr. 1988, pp. 2444-2448, vol. 85.

(Continued)

*Primary Examiner* — Zachary Howard
(74) *Attorney, Agent, or Firm* — Roche Diagnostics Operations, Inc.

(57) ABSTRACT

The present disclosure relates to a method for diagnosing the ischemic state in a subject suffering from acute coronary syndrome who does not fulfilling the diagnostic criteria for a myocardial infarction. The present disclosure also relates to a method for identifying a subject being susceptible to cardiac intervention, wherein the subject suffers from acute coronary syndrome but does not fulfill the diagnostic criteria for a myocardial infarction. The methods of the present disclosure are based on the determination of fms-like tyrosine kinase-1 (sFLT-1) and, optionally, hepatocyte growth factor (HGF) in a sample of said subject. The present disclosure also relates to kits and/or devices for carrying out the methods disclosed herein.

14 Claims, No Drawings

(56) References Cited

OTHER PUBLICATIONS

Ruzgar, Ozcan et al., "The use of human heart-type fatty acid-binding protein as an early diagnostic biochemical marker of myocardial necrosis in patients with acute coronary syndrome, and its comparison with troponin-T and creatine kinase-myocardial band," Heart Vessels, 2006, pp. 309-314, vol. 21.

Scirica, Benjamin M. et al., "Ischemia Detected on Continuous Electrocardiography After Acute Coronary Syndrome, Observations From the MERLIN-TIMI 36 (Metabolic Efficiency With Ranolazine for Less Ischemia in Non-ST-Elevation Acute Coronary Syndrome—Thrombolysis in Myocardial Infarction 36) Trial," Journal of the American College of Cardiology, 2009, pp. 1411-1421, vol. 53, No. 16.

Smith, Temple F. and Waterman, Michael S., "Comparison of Biosequences," Advances in Applied Mathematics, 1981, pp. 482-489, vol. 2.

Thygesen, Kristian et al., "Universal definition of myocardial infarction," European Heart Journal, 2007, pp. 2525-2538, vol. 28.

Tzivoni, Dan and Krucoff, Mitchell W., "Continuous ST-Segment Monitoring in Contemporary Acute Coronary Syndrome Patients, The Magic of MERLIN-TIMI 36," Journal of the American College of Cardiology, 2009, pp. 1422-1424, vol. 53, No. 16.

International Search Report issued Jan. 31, 2011 in Application No. PCT/EP2010/068391, 6 pages.

Heeschen, Christopher et al., "Prognostic Significance of Angiogenic Growth Factor Serum Levels in Patients With Acute Coronary Syndromes," Circulation, 2003, pp. 524-530, vol. 107, No. 4.

Braunwald, Eugene et al., "ACC/AHA 2002 Guideline Update for the Management of Patients With Unstable Angina and Non-ST-Segment Elevation Myocradial Infarction—Summary Article," Journal of the American College of Cardiology, 2002, pp. 1366-1374, vol. 40, No. 7.

Kapur, Navin K. et al., "Elevated Soluble fms-Like Tyrosine Kinase-1 Levels in Acute Coronary Occlusion," Arteriosclerosis and Thrombosis: A Journal of Vascular Biology, 2011, pp. 443-450, vol. 31.

Blakenberg, Stefan et al., "Cytomegalovirus Infection With Interleukin-6 Response Predicts Cardiac Mortality in Patients With Coronary Artery Disease," Circulation, 2001, pp. 2915-2921, vol. 103.

Blankenberg, Stefan et al., "Interleukin-18 Is a Strong Predictor of Cardiovascular Death in Stable and Unstable Angina," Circulation, 2002, pp. 24-30, vol. 106.

* cited by examiner

METHOD FOR DIAGNOSING AND MONITORING CARDIAC ISCHEMIA IN PATIENTS WITH ACUTE CHEST PAIN AND WITHOUT MYOCARDIAL INFARCTION

PRIORITY CLAIM

This application is a continuation of International Application No. PCT/EP2010/068391, filed Nov. 29, 2010, which claims the benefit of European Patent Application No. 09177395.2, filed Nov. 27, 2009, the disclosures of which are hereby incorporated by reference in their entirety.

FIELD OF THE DISCLOSURE

The present disclosure relates to the field of medical diagnostics.

BACKGROUND

An aim of modern medicine is to provide personalized or individualized treatment regimens. Those are treatment regimens which take into account a patient's individual needs or risks. A particularly important risk is the presence of cardiovascular complication, especially of an acute cardiovascular event. Cardiovascular complications belong to the leading causes of morbidity and mortality in the Western hemisphere. For individual treatment of a person who suffers from a cardiovascular complication, a reliable diagnosis has a significant impact on the success of the treatment of said person. This is particularly important for patients showing signs and symptoms of acute coronary syndrome (ACS).

Clinical symptoms of acute coronary syndrome are believed to be caused by acute myocardial ischemia. Patients with chest pain or signs and symptoms of instable angina or acute coronary syndrome (ACS) frequently present to their doctor as an emergency or to the emergency room. Clinical evaluation of these patients includes a medical history specifically directed to evidence of existing cardiovascular disease or their risk factors, analysis of the type of symptoms as described as well as clinical signs associated with acute coronary syndrome such as evidence of pulmonary edema, hypotension and/or Tachy- or bradycardia. Additionally, clinical evaluation often includes performing an electrocardiogram (ECG) and possibly laboratory tests on these patients.

Although acute chest pain is the leading symptom of ACS, it is not specific for cardiovascular disease or ACS. Symptoms of chest pain may originate from vascular disorders such as pulmonary embolism, aortic dissection or pulmonary hypertension or from pulmonary diseases such as pleuritis, pneumonia, tracheobronchitis and spontaneous pneumothorax. Symptoms of acute chest pain may also originate from gastrointestinal disease such as esophageal reflux, peptic ulcer, gallbladder disease and pancreatitis. Additionally, musculoscelatal causes of acute pain may include costochondritis, cervical disc disease, trauma or strain. Herpes zoster may also causes acute chest pain. Even further, panic disorder needs to be considered as differential diagnosis.

SUMMARY OF THE DISCLOSURE

The present disclosure relates to a method for diagnosing the ischemic state and a method for monitoring the course of the severity of the ischemic state in a subject showing signs and symptoms of general acute chest pain or acute coronary syndrome but not fulfilling the diagnostic criteria for a (non ST-elevated) myocardial infarction. Moreover, the present disclosure relates to a method for identifying a subject being susceptible to cardiac intervention and a method of deciding on the intervention. Also comprised are kits and devices for carrying out the methods of the present disclosure. The methods of the present disclosure are based on the determination of soluble fms-like tyrosine kinase-1 (sFLT-1) and optionally hepatocyte growth factor (HGF) in a sample of said subject and comparing the amount of sFLT-1 and, optionally, HGF to at least one reference amount. Also comprised by the present disclosure are kits or devices to carry out the methods of the present disclosure.

The present disclosure provides a method for diagnosing an ischemic state in a subject showing signs and symptoms of acute coronary syndrome but not fulfilling the diagnostic criteria for a myocardial infarction, based on the comparison of the amounts of soluble fms-like tyrosine kinase-1 (sFLT-1) or a variant thereof in a sample of said subject, to at least one reference amount. The method may comprise at least one of the following steps: a) determining the amount of soluble fms-like tyrosine kinase-1 (sFLT-1) or a variant thereof in a sample of said subject, b) comparing the amount of sFLT-1 or a variant thereof determined in step a) to at least one reference amount, and c) diagnosing the ischemic state based on the information obtained in step b) and preferably based on the information obtained in a) and b).

Accordingly, the present disclosure relates to a method for diagnosing an ischemic state in a subject showing signs and symptoms of acute coronary syndrome but not fulfilling the diagnostic criteria for a myocardial infarction, comprising
  a) determining the amount of soluble fms-like tyrosine kinase-1 (sFLT-1) or a variant thereof in a sample of said subject,
  b) comparing the amount of sFLT-1 or a variant thereof determined in step a) to at least one reference amount, and
  c) diagnosing the ischemic state based on the information obtained in step b) and preferably based on the information obtained in a) and b).

Moreover, the present disclosure relates to a method for diagnosing an ischemic state in a subject showing signs and symptoms of acute coronary syndrome but not fulfilling the diagnostic criteria for a myocardial infarction, comprising
  a) comparing the amount of soluble fms-like tyrosine kinase-1 (sFLT-1) or a variant thereof determined in a sample of said subject to at least one reference amount, and
  b) diagnosing the ischemic state based on the information obtained in step a).

Moreover, the present disclosure relates to a method for diagnosing an ischemic state in a subject showing signs and symptoms of acute coronary syndrome but not fulfilling the diagnostic criteria for a myocardial infarction, comprising
  a) diagnosing the ischemic state based on the comparison of the amount of soluble fms-like tyrosine kinase-1 (sFLT-1) or a variant thereof determined in a sample of said subject to at least one reference amount.

The present disclosure also provides a method for monitoring the ischemic state in a subject showing signs and symptoms of acute coronary syndrome but not fulfilling the diagnostic criteria for a myocardial infarction, based on the comparison of the amounts of soluble fms-like tyrosine kinase-1 (sFLT-1) or a variant thereof determined at least at two different points in time in a sample of said subject, to at least one reference amount. The method may comprise at least one of the following steps: a) determining at least at two different points in time the amounts of soluble fms-like tyrosine kinase-1 (sFLT-1) or a variant thereof in a sample of said subject, b) comparing the amounts of sFLT-1 or a variant thereof determined in step a) to at least one reference amount, and c) diagnosing the ischemic state at the at least at two different points in time based on the information obtained in step b) and preferably based on the information obtained in a) and b).

The present disclosure accordingly also relates to a method for monitoring the ischemic state in a subject showing signs and symptoms of acute coronary syndrome but not fulfilling the diagnostic criteria for a myocardial infarction, comprising the steps of:
  a) determining at least at two different points in time the amounts of soluble fms-like tyrosine kinase-1 (sFLT-1) or a variant thereof in a sample of said subject, and
  b) comparing the amounts of sFLT-1 or a variant thereof as determined in step a) to at least one reference amount, and
  c) diagnosing the ischemic state at the at least at two different points in time, based on the information obtained in step b), and preferably based on the information obtained in a) and b), so as to monitor the ischemic state.

Moreover, the present disclosure relates to a method for monitoring an ischemic state in a subject showing signs and symptoms of acute coronary syndrome but not fulfilling the diagnostic criteria for a myocardial infarction, comprising
  a) comparing the amounts of sFLT-1 or a variant thereof determined at least at two different points in time in a sample of the subject to at least one reference amount, and
  b) diagnosing the ischemic state based on the information obtained in step a), so as to monitor the ischemic state.

Moreover, the present disclosure relates to a method for monitoring an ischemic state in a subject showing signs and symptoms of acute coronary syndrome but not fulfilling the diagnostic criteria for a myocardial infarction, comprising
  a) monitoring the ischemic state based on the comparison of the amounts of soluble fms-like tyrosine kinase-1 (sFLT-1) or a variant thereof determined at least at two different points in time in a sample of the subject to at least one reference amount.

In an embodiment of the aforementioned methods of the present disclosure, additionally the amount of hepatocyte growth factor (HGF) or a variant thereof is determined in an additional step aa) in a sample of said subject and compared to at least one reference amount for HGF in step bb). Accordingly, in step c), the ischemic state is diagnosed based on the determined amounts of sFLT-1 or a variant thereof and HGF or a variant thereof and the comparison of the amount of sFLT-1 to at least one reference amount for sFLT-1 and the comparison of the amount of HGF to at least one reference amount for HGF. Preferably, first the amount of sFLT-1 and then the amount of HGF is determined, however is also contemplated that the amounts of sFLT-1 and HGF are determined in any order, i.e. simultaneously, or first sFLT-1 and then HGF, or first HGF and then sFLT-1.

In a further embodiment of the present disclosure, the ischemic state in a subject showing signs and symptoms of acute coronary syndrome, but not fulfilling the diagnostic criteria for a myocardial infarction, is diagnosed by determining the level of hepatocyte growth factor HGF or a variant thereof in a sample of said subject. Likewise, in a further embodiment of the present disclosure, the ischemic state in a subject showing signs and symptoms of acute coronary syndrome but not fulfilling the diagnostic criteria for a myocardial infarction is monitored by determining the amounts of hepatocyte growth factor HGF or a variant thereof in a sample of the said subject, in at least at two different points in time. As disclosed herein and in accordance with the subject disclosure, HGF may act as an independent marker of ischemia delivering information on the ischemia which is, in many cases, at least as good as the information provided by sFLT-1. Accordingly, in some instances of embodiments of the instant disclosure, sFLT-1 gives better information; in some cases, HGF gives better information; and in some cases, the information of both markers can be said to be equal.

In an embodiment of the aforementioned method of the present disclosure, additionally the amount of fms-like tyrosine kinase-1 (sFLT-1) or a variant thereof is determined in an additional step aa) in a sample of said subject and compared to at least one reference amount for fms-like tyrosine kinase-1 (sFLT-1) in step bb). Accordingly, in step c), the ischemic state is diagnosed based on the determined amounts of sFLT-1 or a variant thereof and HGF or a variant thereof and the comparison of the amount of sFLT-1 to at least one reference amount for sFLT-1 and the comparison of the amount of HGF to at least one reference amount for HGF. Preferably, first the amount of HGF and then the amount of sFLT-1 is determined, however is also contemplated that the amounts of sFLT-1 and HGF are determined in any order, i.e. simultaneously, or first sFLT-1 and then HGF, or first HGF and then sFLT-1.

Accordingly, the present disclosure relates to a method for diagnosing an ischemic state in a subject showing signs and symptoms of acute coronary syndrome but not fulfilling the diagnostic criteria for a myocardial infarction, comprising
  a) determining the amount of hepatocyte growth factor HGF or a variant thereof in a sample of said subject,
  b) comparing the amount of HGF or a variant thereof determined in step a) to at least one reference amount, and
  c) diagnosing the ischemic state based on the information obtained in step b), preferably based on the information obtained in a) and b).

Moreover, the present disclosure relates to a method for diagnosing an ischemic state in a subject showing signs and symptoms of acute coronary syndrome but not fulfilling the diagnostic criteria for a myocardial infarction, comprising
  a) comparing the amount of HGF or a variant thereof determined in a sample of said subject to at least one reference amount, and
  b) diagnosing the ischemic state based on the information obtained in step a).

Moreover, the present disclosure relates to a method for diagnosing an ischemic state in a subject showing signs and symptoms of acute coronary syndrome but not fulfilling the diagnostic criteria for a myocardial infarction, comprising
  a) diagnosing the ischemic state based on the comparison of the amount of HGF or a variant thereof determined in a sample of said subject to at least one reference amount.

The present disclosure also relates to a method for monitoring the ischemic state in a subject showing signs and symptoms of acute coronary syndrome but not fulfilling the diagnostic criteria for a myocardial infarction, comprising the steps of
  a) determining at least at two different points in time the amounts of hepatocyte growth factor HGF or a variant thereof in a sample of said subject, and
  b) comparing the amounts of HGF or a variant thereof as determined in step a) to at least one reference amount, and
  c) diagnosing the ischemic state at the at least at two different points in time, based on the information obtained in step b), preferably based on the information obtained in a) and b), so as to monitor the ischemic state.

Moreover, the present disclosure relates to a method for monitoring an ischemic state in a subject showing signs and symptoms of acute coronary syndrome but not fulfilling the diagnostic criteria for a myocardial infarction, comprising a) comparing the amounts of HGF or a variant thereof determined at least at two different points in time in a sample of the subject to at least one reference amount, and b) diagnosing the ischemic state based on the information obtained in step a), so as to monitor the ischemic state.

Moreover, the present disclosure relates to a method for monitoring an ischemic state in a subject showing signs and symptoms of acute coronary syndrome but not fulfilling the diagnostic criteria for a myocardial infarction, comprising a) monitoring the ischemic state based on the comparison of the amounts of HGF or a variant thereof determined at least at two different points in time in a sample of the subject to at least one reference amount.

In some embodiments, the amounts of a cardiac troponin are determined simultaneously with the determination of sFLT-1 and/or the determination of HGF; the determination of the amounts of a cardiac troponin may also precede the determination of sFLT-1 and/or the determination of HGF. The ischemic state of the individual, therefore, may be determined simultaneously with or after troponin determination, by determining the amounts of sFLT-1 and/or HGF or, optionally, the further marker. Accordingly, if the cardiac troponin amount is determined prior to the determination of sFLT-1 and/or HGF, the determination of the amounts of sFLT-1 and/or HGF may be deferred until the amount of the cardiac troponin is known, and in case the troponin amount is lower than the amount which is generally recognized in the art as being indicative for a myocardial infarction MI, such as a NSTEMI, the amount of sFLT-1 and/or HGF may be determined. The amount of the cardiac troponin may even be zero, i.e., not detectable with the tests presently available.

In a further embodiment, an ECG of the respective subject is determined in conjunction with the determination of sFLT-1 and/or the determination of HGF; measuring the ECG may also precede the determination of sFLT-1 and/or the determination of HGF. The ischemic state of the individual, therefore, may be determined simultaneously with or after measuring an ECG, by determining the amounts of sFLT-1 and, optionally, HGF. Accordingly, if the ECG measurement is carried out prior to the determination of sFLT-1 and/or HGF, the determination of the amounts of sFLT-1 and/or HGF may be deferred until the ECG is recorded. In some cases in which the subject's ECG does not show a ST elevation, the amount of sFLT-1 and/or HGF may be determined. In some cases in which the ECG shows a ST elevation, the subject may be considered to have suffered from a STEMI disclosure.

In the context of the foregoing, furthermore, the determination of the amounts of a cardiac troponin and/or measuring the ECG can be carried out simultaneously or sequentially, including the determination of sFLT-1 and/or HGF as laid out above.

According to some embodiments, the present disclosure provides a method for diagnosing an ischemic state in a subject. According to some embodiments the method comprises the steps of contacting, in vitro, a portion of a sample from a subject with a ligand having an affinity for one of a soluble fms-like tyrosine kinase-1 and variant thereof; calculating an amount of the one of soluble fms-like tyrosine kinase-1 and variant thereof based on said step of contacting; providing a diagnosis of cardiac dysfunction if the amount of the one of sFLT-1 and the variant thereof is greater than about 92 pg/ml.

In some embodiments the method further comprises the steps of contacting, in vitro, a portion of the sample with a ligand having an affinity for one of hepatocyte growth factor and a variant thereof; and calculating an amount of the one of hepatocyte growth factor and the variant thereof based on said step of contacting, wherein said step of providing further comprises the amount of the one of hepatocyte growth factor and the variant thereof being greater than 0.62 pg/ml.

In even further embodiments, the method may comprise the steps of contacting, in vitro, a portion of the sample with a ligand having an affinity for one of NT-proANP and a variant thereof; and calculating an amount of the one of NT-proANP and the variant thereof based on said step of contacting, wherein said step of providing further comprises providing a diagnosis of circulatory impairment if the amount of the one of NT-proANP and the variant thereof is greater than about 1320 pg/ml.

In some embodiments, the steps of calculating and providing are performed by a computing device. In some further embodiments, the ligand comprises an antibody. In even further embodiments, the steps of contacting are performed for at least two different points in time with at least two different samples of the subject and said step of calculating is also performed for the at least two different points in time.

Additionally, some embodiments of the instant disclosure provide a kit for carrying out the methods of the embodiments disclosed herein. In some embodiments, the kit may include a ligand having an affinity for one of a soluble fms-like tyrosine kinase-1 and variant thereof; and a means for calculating the amount of the one of soluble fms-like tyrosine kinase-1 and variant thereof in a sample of a subject.

In some embodiments, the kit may also include ligand having an affinity for one of hepatocyte growth factor and a variant thereof and one of NT-proANP and a variant thereof. In some embodiments, the ligand may be an antibody and the means for calculating may be a florescent label bound to the ligand, the label being detectable and quantifiable.

The above-described embodiments of the various aspects of the disclosure may be used alone or in any combination thereof without departing from the scope of the disclosure.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Clinically cardiac acute chest pain can be identified by clinical features such as retrosternal chest pressure or burning or heaviness radiating occasionally to neck, jaw, epigastrium, shoulders or left arm. Severity of acute chest pain frequently increases from angina to unstable angina and myocardial infarction. Precipitating causes include physical and emotional stress or cold. Severity is also associated with duration of chest pain ranging from less than 2 minutes in angina to more than 30 minutes in myocardial infarction. While these symptoms are fairly characteristic in severe cases, mild cases of cardiac chest pain are often difficult to separate from non-cardiac causes. (see, for example, Braunwald Heart Disease, Chapter 49, page 1196).

Patients with signs of acute coronary syndrome have a significantly increased risk of experiencing non reversible cardiac injury or even cardiac death and, therefore, need to be identified among the patients with nontraumatic chest symptoms (see, Morrow et al., National academy of clinical biochemistry guidelines: Clinical characteristics and utilization of biochemical markers in acute coronary syndrome, 2007, Circulation; 115; 356-375). An acute coronary syndrome may be caused by a sudden blockage in a coronary artery, significantly reducing or cutting off the blood supply to connected areas of the myocardium (heart muscle) and resulting in ischemia (lack of blood supply).

Heart tissue becomes necrotic in case of significant and/or persisting ischemia. Myocardial infarction (MI), also termed heart attack, is known as cell necrosis in the myocardium (heart tissue) from ischemia, as described by The Joint ESC/ACCF/AHA/WHF Task Force for the Redefinition of Myocardial Infarction (The Joint European Society of Cardiology/American College of Cardiology Committee: Universal definition of myocardial infarction, European Heart Journal (2007), 28, 2525-2538).

A thrombus is a common cause of a blocked coronary artery which may already be partially narrowed by atheromas. An atheroma may rupture or tear, releasing substances that make platelets stickier and encouraging thrombi formation. In many cases, the thrombus dissolves on its own, typically within a day or so. However, by this time, some heart damage may already have occurred.

Evaluation of medical history (history of coronary artery disease CAD) is one criterion for the diagnosis of patients exhibiting symptoms of ACS (e.g. chest pain for more than 20 min). These patients are furthermore diagnosed using electrocardiogram (ECG) and may undergo troponin testing. In cases of an initially nondiagnostic ECG at presentation and a Troponin test result not meeting the diagnostic criteria of non ST-elevation myocardial infarction, these procedures may be repeated after 4-8 hours. In cases where the ECG and troponin determination continue not to meet the diagnostic criteria of myocardial infarction, the patient may be discharged with the a diagnosis indicating an exclusion of myocardial infarction.

The electrocardiogram (ECG) can provide important information for the diagnosis. Particularly, if the ECG shows elevated ST segments, a ST elevated myocardial infarction (STEMI) may be diagnosed. If the ECG does not show elevated ST segments, a non ST elevated MI (NSTEMI) may be diagnosed when cardiac Troponin is detected in a sample of the respective patient. Patients without a diagnostic ECG and with a cardiac Troponin level lower than the amount that is indicative for a myocardial infarction are suspected to have unstable angina pectoris (UAP). Unstable angina and NSTEMI are considered to be closely related conditions, sharing a similar clinical presentation. However, they differ in their severity. NSTEMI may be distinguished from unstable angina by ischemia causing irreversible myocardial damage which is detectable by biomarkers of myocardial necrosis (Morrow et al., loc. cit.). In all described cases, e.g., STEMI, NSTEMI and UAP, the patient is generally treated according to the diagnosis.

In cases in which the ECG (electrocardiogram) shows a ST elevation, a ST elevation myocardial infarction may be diagnosed and the patient may be considered for evaluation of reperfusion therapy. If the ECG remains nondiagnostic, which may include ST or T wave changes in the ECG, a troponin T or I result diagnostic for NON ST elevation myocardial infarction may reveal a final diagnosis. However, a majority of patients with chest pain or signs and symptoms of acute coronary syndrome present with a nondiagnostic ECG and a Troponin result non meeting the criteria of Non STEMI according to current recommendations (see, for example, The Joint European Society of Cardiology/American College of Cardiology Committee: Universal definition of myocardial infarction, European Heart Journal (2007), 28, 2525-2538). Such patients may have myocardial infarction but frequently present within the first 4-6 hours after onset of signs/symptoms (i.e., before the cardiac specific necrosis marker starts to be released from the myocardium and circulates in increased amounts in the serum/plasma). Another group of patients may also have chest pain completely unrelated to a cardiac disorder and therefore will not develop characteristic ECG changes or cardiac necrosis as indicated by increased troponin amounts. Such patients may be finally diagnosed with non-cardiac chest pain. In a subgroup of patients testing for myoglobin (myoglobulin) and/or heart fatty acid binding protein (H-FABP) will present evidence for a myocardial infarction which may be diagnosed later by an increase in troponin possibly associated with changes in the ECG.

As indicated current efforts in patients with chest pain, or presenting with other symptoms, target the identification of myocardial infarction or its exclusion. So far, the electrocardiogram and troponins have been the key points of positive diagnosis of myocardial infarction or its exclusion.

Troponin is a structural protein of the myocardium and is released upon necrosis or apoptosis of myocardial tissue. In addition, troponins are considered to be specific for myocardial tissue and, thus, an increase of troponin levels in the circulation is considered an indicator of myocardial infarction. Unfortunately, troponin levels increase only 4 to 6 hours after a myocardial infarction has occurred and thus results in a delayed diagnosis. This delayed recognition of myocardial infarction may result in delayed treatment e.g. by PCI and accordingly, the myocardium may become necrotic which could have been saved by earlier intervention.

Attempts to overcome this delay in recognition of myocardial infarction have included the use of myoglobin or heart fatty acid binding protein. Heart fatty acid binding protein (H-FABP) is a low molecular weight cytoplasmic protein and present abundantly in the myocardium. It has been recognized that H-FABP is already released from the myocardium when the myocardium loses its function, which is well before it becomes necrotic. It has been clearly shown that H-FABP levels beyond 5700 pg/ml are indicative of a future increase of troponin and myocardial infarction and a H-FABP level below 2500 pg/ml was found not to be associated with MI, see WO 2008/145689.

Similarly, myoglobin represents another molecule which enters the circulation early after a myocardial infarction. It has been shown that a myoglobin concentration above 77 ng/ml is indicative of future troponin increase and, thus, of myocardial infarction. In contrast a myoglobin concentration below 55 ng/ml makes the development of a future troponin increase and, thus, of infarction unlikely. (see, for example, WO 2009/033831).

Accordingly, the determination of myoglobin and/or H-FABP in serum or plasma is useful to compensate for some of the limitation of troponin determination, (i.e. the troponins' late appearance in the circulation after 4-6 hours), and represents an aid in early diagnosis of MI and thus allows intervention if myoglobin or heart fatty acid binding protein predict the development of troponin.

Patients presenting with chest pain or symptoms of acute coronary syndrome are often discharged if symptoms resolve and they do not meet current diagnostic criteria of MI. Such patients may, however, still be at increased risk of myocardial infarction as was recently shown by continuous ECG recordings (see, Tvivoni et al J. Am Coll Cardiol 53, 2009, 1422-24, Scirica Am Coll Cardiol 53, 2009, 1411-1421). In this study, an ST depression of as short as 1 minute and as small ½ mm indicated temporary ischemia and poor outcome. This method is, however, not easily applicable and requires computer assisted technology and can only be done prospectively. This stresses the importance of the recognition of ischemia, an event which precedes necrosis and metabolic myocardial abnormalities.

The present disclosure provides a method for identifying ischemia in patients presenting with chest pain or signs or symptoms of acute coronary syndrome, to determine the extent of ischemia, its duration as well as functional abnormalities associated with ischemia. These methods should also allow the exclusion of ischemia and further classification of patients presenting with chest pain or symptoms of acute coronary syndrome so as to provide an improved diagnostic and therapeutic work up.

The instant disclosure also provides diagnostic and prognostic means and methods for reliable and quick diagnosis of ischemia in a subject who shows signs and symptoms of an acute coronary syndrome and who has a cardiac Troponin amount lower than the level indicative for a myocardial infarction. In some embodiments, the individual may also have a non diagnostic ECG, such as an ECG not showing an ST elevation. In some embodiments, the means and methods of the instant disclosure may allow a diagnosis not only of ischemia, but should also permit an assessment of the degree of ischemia and its changes, and aid in the discrimination of cardiac and non-cardiac causes of chest pain. In further embodiments, some methods of the instant application also help to identify a subgroup of patients with cardiac chest pain who display levels of further cardiac biomarkers such as troponin, but also, as the case may be, myoglobin or H-FABP below the diagnostic reference amount characteristic for ischemia. Furthermore, embodiments of the instant disclosure also provide for quantification of ischemia, for example, in cases of enduring or continuing periods of ischemia and in the event of recurrent ischemic episodes. Additionally, methods and means of the subject disclosure may also permit the identification of a subject as being susceptible to cardiac intervention, to decide if a cardiac intervention of the subject is appropriate and, in the affirmative, which therapy is to be selected. As detailed herein, the various embodiments of the method and means provided herein allow for avoiding at least some of the drawbacks of the current techniques as laid out above.

Evaluation of medical history (history of coronary artery disease CAD) is one criterion for the diagnosis of patients exhibiting symptoms of ACS (e.g. chest pain for more than 20 min). These patients are furthermore diagnosed using electrocardiogram (ECG) and may undergo troponin testing. In cases of an initially nondiagnostic ECG at presentation and a Troponin test result not meeting the diagnostic criteria of non ST-elevation myocardial infarction, these procedures may be repeated after 4-8 hours. In cases where the ECG and troponin determination continue not to meet the diagnostic criteria of myocardial infarction, the patient may be discharged with the a diagnosis indicating an exclusion of myocardial infarction. The latest criteria for the diagnosis of myocardial infarction MI are described by The Joint ESC/ACCF/AHA/WHF Task Force for the Redefinition of Myocardial Infarction (The Joint European Society of Cardiology/American College of Cardiology Committee: Universal definition of myocardial infarction, I.c.).

Embodiments of the instant method may comprise in vitro methods. Moreover, embodiments may comprise steps in addition to those explicitly mentioned above. For example, further steps may relate to sample pre-treatments or evaluation of the results obtained by the method. Embodiments of the present disclosure may be also used for monitoring, confirmation, and subclassification of a diagnosis. Additionally, embodiments may be carried out manually or assisted by automation. In some exemplary embodiments, step (a), (b) and/or (c) may in total or in part be assisted by automation, e.g., by a suitable robotic and sensory equipment for the determination in step (a) or a computer-implemented comparison in step (b).

As used herein, the phrase "signs and symptoms of acute coronary syndrome" relates, on the one hand, to those signs which may indicate ACS, but which may also occur in diseases other than ACS. Accordingly, this term includes those signs which cannot unambiguously be related to the occurrence of ACS, but which indicate a probability for the occurrence of ACS such that further examination for confirmation (rule in/rule out) is mandatory. One example of such sign is chest pain. Of course, chest pain may as well originate from vascular disorders such as pulmonary embolism, aortic dissection or pulmonary hypertension or from pulmonary diseases such as pleuritis, pneumonia, tracheobronchitis and spontaneous pneumothorax; from gastrointestinal disease such as esophageal reflux, peptic ulcer, gallbladder disease and pancreatitis, musculoskeletal causes of acute pain include costochondritis, cervical disc disease, trauma or from strain. Herpes zoster also causes acute chest pain. These forms of chest pain are often referred to as "non-cardiac chest pain". On the other hand, the term relates to cardiac acute chest pain giving rise to symptoms like retrosternal chest pressure or burning or heaviness radiating occasionally to neck, jaw, epigastrium, shoulders or left arm. Severity of acute chest pain frequently increases from angina to unstable angina and myocardial infarction. Precipitating causes include physical and emotional stress or cold. Severity may also be associated with duration of chest pain ranging from less than 2 minutes in angina to more than 30 minutes in myocardial infarction. While these symptoms are fairly characteristic in severe cases, mild cases of cardiac chest pain might be difficult to separate from non-cardiac causes. Further known symptoms of ACS are epigastric, arm, wrist or jaw discomfort or pain, unexplained nausea or vomiting, persistent shortness of breath, weakness, dizziness, light-headedness or syncope as well as any combinations thereof.

The above-cited symptoms may, however, in many cases not appear sufficiently specific as to permit a safe and correct diagnosis (or avoid a false diagnosis) of ACS. Chest pain, for example, may not be located unambiguously. Another group of patients may have chest pain completely unrelated to a cardiac disorder and therefore will not develop characteristic ECG changes or cardiac necrosis as indicated by increased troponin amounts. Such patients will be finally diagnosed with non-cardiac chest pain. A cardiologist may be capable of ruling in or ruling out the occurrence of ACS, based on the identification of symptoms typical for ACS and neglecting those symptoms not typical for ACS. However, this method can be error-prone, and modern cardiology requires the determination of cardiac troponins and ECG, further to the interpretation of symptoms for the respective individual (and the evaluation of medical history). Embodiments of the present disclosure are useful for those individuals having signs and symptoms of ACS, in particular chest pain, wherein the signs/symptoms, in particular chest pain, do not permit an unambiguous diagnosis of ACS (based on current approaches) due to being possibly related to ACS, but possibly also being related to disorders other than ACS; however, the symptoms, in particular the chest pain, require a further diagnosis/evaluation of the underlying diseases, in order to rule in or rule out ACS. As the case may be, it is also possible that the individual to which the method of the present disclosure is applied shows symptoms which are unambiguous for ACS, e.g. strong chest pain radiating to the arm or shoulder.

The term "diagnosing" as used herein means assessing, identifying, evaluating or classifying the ischemic state in a subject showing the signs and symptoms of coronary syndrome and having a cardiac troponin amount lower than the amount indicative for a MI, in particular if the subject suffers from an ischemic state leading to a reversible cardiac dysfunction or to a non-reversible cardiac injury. The term "diagnosing" also refers to distinguishing, in subjects showing the signs and symptoms of acute coronary syndrome and preferably having a cardiac troponin amount lower than the amount indicative for a MI, between a physiologically healthy subject and a subject suffering from ischemia which, as the case may be, will lead to a reversible cardiac dysfunction to non-reversible cardiac injury.

The diagnosis and the criteria applied for the diagnosis of ACS are generally known in the art and inter alia include the evaluation of medical history (history of coronary artery disease CAD) and chest pain for more than about 20 min.

As used herein, the phrase "a subject showing signs and symptoms of acute coronary syndrome not fulfilling the diagnostic criteria for a myocardial infarction" encompasses a subject showing signs and symptoms of acute coronary syndrome which may or may not be associated with the occurrence or diagnosis of a myocardial infarction (e.g., the displayed signs and symptoms do not suffice to diagnose myocardial infarction without leaving doubts on the diagnostic result). The criteria for the diagnosis of myocardial infarction are described by The Joint ESC/ACCF/AHA/WHF Task Force for the Redefinition of Myocardial Infarction (The Joint European Society of Cardiology/American College of Cardiology Committee: Universal definition of myocardial infarction, I.c.), which have already been summarized beforehand.

In some cases, the cardiac troponin amount may be determined and the subject may display an amount of cardiac Troponin lower than the amount that is indicative for a myocardial infarction. Also, an electrocardiogram (ECG) may be recorded in the subject and the ECG may fail to meet the criteria for myocardial infarction, for example the patient may fail to meet the criteria for non ST-elevation MI. In some cases, the level of a cardiac troponin may be determined and an ECG may be recorded and these two parameters may fail to meet the criteria for myocardial infarction, (i.e., the determined amount of troponin may be lower than the amount indicative for a myocardial infarction and/or the ECG, for example). In cases of an ECG which fails to meet the criteria for myocardial infarction at presentation and a Troponin test result which does not meet the diagnostic criteria of (non ST-elevation) myocardial infarction, this procedure may be repeated, for example after about 4-about 8 hours. In case the ECG and troponin determination continue not to meet the diagnostic criteria of myocardial infarction, the patient may be discharged with the diagnosis of exclusion of myocardial infarction.

The term "ischemia" or "ischemic state", as used herein, relates to the state of an impaired blood supply not sufficient for metabolic needs, in particular not sufficient for oxygen supply, to the affected tissue. Ischemia may be associated with, lead to or cause an altered myocardial function depending on the extent of ischemic myocardium and duration of ischemia. Myocardial function normalizes rapidly after a single episode of ischemia lasting less than 2 minutes. As ischemia increases in duration and/or severity, there is a temporal delay in recovery of function that occurs, despite the fact that blood flow has been restored. A 15 minute occlusion of a vessel results, e.g., in a 6 h altered myocardial function although the blood flow is restored. This reversible event is not associated with myocardial necrosis. The term "ischemia" or "ischemic state" may encompass a reversible cardiac dysfunction and a non-reversible cardiac injury as well as a process leading to, being associated with or causing a reversible cardiac dysfunction or a non-reversible cardiac injury. Ischemia or the ischemic state may also encompass a cardiac injury which is associated with, leads to, or causes a myocardial infarct.

The phrase "reversible cardiac dysfunction" relates to an impaired pumping capacity or activity of the heart, which is fully reversible and preferably occurs without leaving any significant structural deterioration to the heart, including necrosis of a significant number of cardiomyocytes. For example, the impaired pumping capacity or activity may not cause any significant injury to the subject's body. A reversible cardiac dysfunction may be immediately reversible, e.g., within a few seconds or minutes like in cases of very short ischemic periods. Further examples of reversible cardiac dysfunctions include cardiac stunning. In these cases, reversibility may be delayed for hours or days.

If a significant proportion of the myocardium is ischemic this may result in wall stretch and the rapid increase of natriuretic peptides.

In an exemplary embodiment of the present disclosure, the amount of a natriuretic peptide, i.e. a BNP-type peptide from the group BNP and NT-proBNP or an ANP-type peptide from the group ANP and NT-proANP is determined. In some embodiments, an ANP-type peptide, such as a NT-proANP, is determined, in order to diagnose a possible circulatory impairment of the subject.

Although not causally related to ischemia, an elevation of the amounts of the ANP type natriuretic peptides relative to a reference amount indicates an ischemic state in certain regions of the myocardium which leads to an elevated pumping requirement for the non ischemic myocardium and, in consequence, to a circulatory impairment.

In some embodiments of the present disclosure, the determination of ANP-type natriuretic peptides is performed, for example NT-proANP, although some embodiments may include the determination of BNP-type natriuretic peptides, like NT-proBNP instead of or in combination with ANP-type natriuretic peptides. ANP type peptides generally involve a fast release. For example, following an increase in cardial pressure and volume (wall stretch), the amount of NT-proANP increases within a period in time of 15 to 60 minutes, allowing a rapid diagnosis of a circulatory dysfunction. BNP type natriuretic peptides, on the other hand, in particular NT-proBNP, increase within a period in time of 4 to 6 hours following an increase in cardial pressure and volume (wall stretch).

Circulatory impairment, according to the instant disclosure, may either be associated with or caused by the formation of ischemic regions in the myocardium which have retained their metabolism, or by stunned myocardium regions (having a lowered metabolism and pumping at a lower performance than fully functional myocardium, without exceeding the stunned myocardium's long term pumping performance), for example. A reduced pumping capacity or activity of the ischemic and/or stunned myocardium, may cause the remaining (unimpaired) myocardium to have to ensure the body's need for blood supply and may have to over perform in some cases.

In some embodiments of the present disclosure, subjects having stunned myocardium and/or having suffered from STEMI can be ruled out by determining the amount of H-FABP and/or myoglobin. In general, such embodiments may comprise the determination of H-FABP and/or myoglobin, after determining a cardiac troponin and/or measuring an ECG, and before determining the amounts of sFLT-1 and, optionally, HGF in steps a) and b) of the method of the present disclosure, in order to determine if the subject has suffered from a myocardial infarction, in particular a NSTEMI.

In a stunned myocardium, myocardial function may be depressed at rest but myocytes may remain viable. LV dysfunction may be reversible in stunning. Stunned myocardium is most commonly observed after a transient period of ischemia followed by reperfusion (depressed function at rest but preserved perfusion). The ischemic episodes can be single or multiple, brief or prolonged, but never severe enough to result in injury.

The phrase "non-reversible cardiac injury" is generally known in the field and preferably relates to a cardiac injury with is associated with cell death, preferably necrosis of cardiomyocytes, for example by necrotic process.

An amount of H-FABP and/or myoglobin, in a sample of a subject as defined in the present disclosure which is larger than the reference amount for ruling in the occurrence of MI is indicative for the recent occurrence of MI in said subject. An amount of myoglobin and, optionally, H-FABP in a subject as defined in the present disclosure lower than the reference amount for ruling out the occurrence of MI may be an indicator that a MI infarction has not occurred recently; in the latter case the subject might suffer from UAP. It is to be understood in the context of the present disclosure that subjects as defined in the present disclosure whose myoglobin amount is between the above mentioned reference amounts (the reference amount for ruling in the recent occurrence of MI and the reference amount for ruling out the recent occurrence of MI) may be required to be diagnosed again. Preferably, this may be also done for subjects in which both the amount of myoglobin and H-FABP are determined, wherein both amounts do not correspond, e.g. one amount is larger (or lower) than the respective reference amount, whereas the other amount is not larger (or lower) than the respective reference amount. Particularly, a myoglobin amount in a subject as defined in the present disclosure of larger than about 77 ng/ml indicates a recent occurrence of MI (rule in), whereas an amount of less than about 55 ng/ml indicates that a MI did not occur recently (rule out). Moreover, the sensitivity and specificity of the diagnosis based on the determination of myoglobin in a sample of a subject as defined in the present disclosure is even more increased when in addition to the amount of myoglobin, the amount of H-FABP is determined in a sample of said subject and compared to at least one reference amount for H-FABP. For example, an H-FABP amount in a subject as defined in the present disclosure of larger than about 5700 pg/ml indicates a recent occurrence of MI (rule in), whereas an amount of less than about 2500 pg/ml indicates that a MI did not occur recently (rule out).

The phrase "diagnosing circulatory impairment" relates to assessing whether in a subject as defined in the present disclosure, i.e. a subject, not suffering from ACS and having a ANP type peptide, such as NT-proANP amount higher than the amount that is considered as being indicative for a healthy subject, a circulatory impairment has occurred or not. The phrase "circulatory impairment" relates to the impaired ability or activity of the heart (myocardium) or region thereof to pump the amount of blood through the circulation which is required to ensure a supply of tissue with sufficient blood for metabolic needs. In order to compensate for the impaired ability, the myocardium has to perform harder, resulting in enhanced wall stress (and release of NT-proANP). For example, a certain region of the myocardium is affected by ischemia, resulting in an impaired pumping capacity of the affected region. To ensure a sufficient blood supply, the pumping performance is augmented, in particular of those myocardium regions which are not effected and which have retained their full pumping capacity. However, due to having to over perform, NT-proANP expression may be stimulated.

In order to compensate for the lack of blood supply, the heart has to perform harder than usually required, resulting in general into an enhanced stress on the heart's walls (because the heart has to pump harder). Such an impairment is not harmful as long as the underlying cause is eliminated before an irreversible cardiac injury occurs. Various reasons for circulatory impairment may exist.

The term "subject" as used herein relates to animals, preferably mammals, and, more preferably, humans.

The term "simultaneously" as used herein relates to carrying out an activity, for example a determination of a marker used in the context of the present disclosure, at the same point in time. This preferably includes measurements wherein the determination of one marker is slightly deferred over the determination of another marker, e.g. for seconds or a few minutes, e.g. 1 minute, 2, 3, 4, 5, 6, 7, 8, 9 or 10 minutes. It is essential that the determination of the later marker is not deferred in a way that its amounts may change to an extent such that a different diagnosis will result. "Determining a marker" relates to the taking of the body fluid sample in which the amount of the marker is determined, or the determination and perception of the marker amount, or both.

The phrase "determining (the amount of a marker) at least at two different points in time" as used herein is meant to encompass the determination of the marker amount in intervals, wherein the second and each further sample will be taken in an interval which ensures an effective monitoring of the ischemic state. In general, the interval between each sample is about 15 minutes, about 30 minutes, about 45 minutes, about 1 hour, about 90 minutes, about 2 hours, about 3, 4, 5, or 6 hours. For example, the initial sample is taken about 1 hour after the onset of symptoms of acute coronary syndrome or immediately after the presentation of the subject to the physician, and each further sample is taken about 1 hour after the initial samples. The number of samples taken will depend on the evaluation of the ischemia.

The phrase "acute coronary syndrome" (ACS) and the criteria for diagnosing ACS are understood and known to the person skilled in the art. The term relates to a constellation of clinical symptoms caused by acute myocardial ischemia. The ischemia itself results from the disruption of an atherosclerotic plaque in a coronary artery. It is known in the art that ACS may be accompanied by symptoms such as epigastric, arm, wrist or jaw discomfort or pain, in particular chest pain, whereby in particular, the chest pain lasts for longer than 20 minutes and may radiate to the arm, back or shoulder. Further symptoms of an acute cardiovascular event may be unexplained nausea or vomiting, shortness of breath, weakness, dizziness, light-headedness, sweating or syncope as well as any combinations thereof. Generally, these clinical symptoms, especially chest pain, occur suddenly; they may appear at rest or after minimal exertion. Moreover, in the context of the present disclosure, the phrase "acute coronary syndrome" may also relate to suspected, assumed, or possible ACS, as these terms are frequently used for patients which show signs and symptoms consistent with ACS, and but for which the diagnosis has not been conclusively established (see Morrow, loc. cit.). ACS patients can show unstable angina pectoris (UAP) or these individuals can suffer from a myocardial infarction (MI). MI can be an ST-elevated MI (STEMI) or a non-ST-elevated MI (NSTEMI). MI is classified as belonging to coronary heart diseases CHD and is preceded by other events also classified as belonging to CHD, like unstable angina pectoris UAP. Symptomatic for UAP is chest pain which is relieved by sublingual administration of nitroglycerine. UAP is caused by a partial occlusion of the coronary vessels leading to hypoxemia and myocardial ischemia. In case, the occlusion is too severe or total, an irreversible myocardial necrosis (which is the pathological state underlying myocardial infarction) results. Generally, STEMI is diagnosed by electrocardiography, in case the electrocardiogram (ECG) show ST-segment elevation. The determination of a cardiac Troponin amount at least six hours after the onset of symptoms of ACS allows for differentiating UAP and NSTEMI. If the Troponin amount is elevated (indicating myocardial damage) a NSTEMI is assumed. MI may occur without obvious symptoms, i.e. the subject does not show any discomfort, and the MI is not preceded by stable or unstable angina pectoris. The occurrence of an MI can be followed by a left ventricular dysfunction (LVD).

The phrase "cardiac Troponin," refers to all Troponin isoforms expressed in cells of the heart and, for example the subendocardial cells. These isoforms are well characterized in the art as described in Anderson 1995, Circulation Research, vol. 76, no. 4: 681-686 and Ferrieres 1998, Clinical Chemistry, 44: 487-493, for example. Cardiac Troponin may refer to Troponin T and/or Troponin I, and, most preferably, to Troponin T. It is to be understood that isoforms of Troponins may be determined in the method of the present disclosure together, i.e. simultaneously or sequentially, or individually, i.e. without determining the other isoform at all. Amino acid sequences for human Troponin T and human Troponin I are disclosed in Anderson, loc cit and Ferrieres 1998, Clinical Chemistry, 44: 487-493.

The phrase "cardiac Troponin" encompasses also variants of the aforementioned specific Troponins, e.g., Troponin I and Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present disclosure comprises an amino acid sequence which differs due to at least one amino acid substitution, deletion and/or addition wherein the amino acid sequence of the variant will generally still be at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific Troponin, generally over the entire length of the specific troponin. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. In some embodiments, the cardiac troponin variants will have immunological properties (i.e., epitope composition) comparable to those of human troponin T or troponin I. Thus, the variants are recognizable by the aforementioned means or ligands used for determination of the amount of the cardiac troponins. Such fragments may be, e.g., degradation products of the Troponins, for example. Further included are variants which differ due to posttranslational modifications such as phosphorylation or myristylation. Also, the biological property of troponin I and its variant comprises the ability to inhibit actomyosin ATPase or to inhibit angiogenesis in vivo and in vitro, which may be detected, for example, based on the assay described by Moses et al. 1999 PNAS USA 96 (6): 2645-2650. The biological property of troponin T and its variant is the ability to form a complex with troponin C and I, to bind calcium ions or to bind to tropomyosin, for example if present as a complex of troponin C, I and T or a complex formed by troponin C, troponin I and a variant of troponin T.

The phrase "cardiac Troponin amount" as used herein relates to the concentration of a cardiac Troponin, such as TnT. The term may relate to the concentration of a cardiac Troponin in a plasma or serum sample of a subject. The phrase "cardiac Troponin lower than the amount that is indicative for a myocardial infarction" may relate to any cardiac Troponin amount starting from and including zero and which is detectable by means and methods known the art, e.g. by commercially available cardiac Troponin assays. The phrase "cardiac Troponin amount which is detectable" may also relate to a concentration that is equal or larger than the lowest detection limit of the assay used for determining the Troponin amount. The Troponin amount which is detectable may relate to any concentration that is equal or larger than 0.001 ng/ml, 0.002 ng/ml, 0.005 ng/ml, 0.0075 ng/ml, or 0.01 ng/ml. In some embodiments of the instant application, the cardiac Troponin amount which is detectable may relate to any concentration that is equal or larger than 0.002 ng/ml. The term "Troponin amount which is indicative for myocardial infarction" may relate to a commonly accepted Troponin concentration that indicates a myocardial infarction.

In some embodiments, Troponin T was tested with the high sensitive Troponin T Test using the ELECSYS 2010 Analyser (Roche Diagnostics, Mannheim, Germany). The test was carried out according to the instructions of the manufacturer. The test has a measuring range from 3-10.000 ng/ml or pg/ml. The precision of the test was found to be between 0.8 to 2.6 percent, depending on the troponin concentration in the sample.

In some embodiments, the amount of the biomarker determined in the sample, such as the amount of cardiac Troponin, considered as being indicative for myocardial infarction relates to a concentration that is above the $95^{th}$, and in some cases above the $99^{th}$ percentile concentration of a suitable reference population (cut-off score). This amount is based upon a recommendation that was made by The Joint ESC/ACCF/AHA/WHF Task Force for the Redefinition of Myocardial Infarction (The Joint European Society of Cardiology/American College of Cardiology Committee: Universal definition of myocardial infarction, I.c.) Suitable reference populations and a determination of the $95^{th}$ and $99^{th}$ percentile concentration are selected based on skill known in the art. It is to be understood that this concentration may differ based on the used assay for determining the cardiac Troponin concentration and based on the selected reference population. Cardiac Troponin amounts indicative for MI in the context of the present disclosure may be, but are not limited to an amount of at least about 0.05 ng/ml, of at least about 0.075 ng/ml, of at least about 0.099 ng/ml, of at least about 0.1 ng/ml, of at least about 0.2 ng/ml and of at least about 0.3 ng/ml.

In an exemplary embodiment of the methods of the present disclosure, the Troponin amount, for example the Troponin T amount, in a subject showing the signs and symptoms of acute coronary syndrome and having a cardiac Troponin amount lower than the amount that is considered as being indicative for a myocardial infarction (as defined in this application) is equal or larger than about 0.002 and lower than about 0.1 ng/ml. The 99$^{th}$ percentile calculated according to the requirements of The Joint ESC/ACCF/AHA/WHF Task Force for the Redefinition of Myocardial Infarction, Ic., was 0.14 ng/ml which comprises an amount indicative for MI according to the instant disclosure.

The phrase "soluble (s)FLT-1" as used herein refers to polypeptide which is a soluble form of the VEGF receptor FLT1. It was identified in conditioned culture medium of human umbilical vein endothelial cells. The endogenous soluble FLT1 (sFLT1) receptor is chromatographically and immunologically similar to recombinant human sFLT1 and binds [125I] VEGF with a comparable high affinity. Human sFLT1 is shown to form a VEGF-stabilized complex with the extracellular domain of KDR/Flk-1 in vitro. sFLT1 may refer to human sFLT1. Human sFLT1 can be deduced from the amino acid sequence of Flt-1 as shown in Genebank accession number P17948, GI: 125361. An amino acid sequence for mouse sFLT1 is shown in Genebank accession number BAA24499.1, GI: 2809071. Moreover, it is to be understood that a variant as referred to in accordance with the present disclosure shall have an amino acid sequence which differs due to at least one amino acid substitution, deletion and/or addition wherein the amino acid sequence of the variant is still, at least 50%, 60%, 70%, 80%, 85%, 90%, 92%, 95%, 97%, 98%, or 99% identical with the amino sequence of the specific sFLT1. Variants may be allelic variants, splice variants or any other species specific homologs, paralogs, or orthologs. Moreover, the variants referred to herein include fragments of the specific sFLT1 or the aforementioned types of variants as long as these fragments have the essential immunological and biological properties as referred to above. The sFLT-1 variants have immunological properties (i.e. epitope composition) and/or biological properties comparable to those of human sFLT-1. Thus, the variants are recognizable by the aforementioned means or ligands used for determination of the amount of sFLT-1. Such fragments may be, e.g., degradation products of sFLT1. Further included are variants which differ due to posttranslational modifications such as glycosylation, phosphorylation or myristylation. The biological property of sFLT-1 comprises the ability to bind to VEGF with a high affinity and/or to form a VEGF-stabilized complex with the extracellular domain of KDR/Flk-1.

In another embodiment of the present disclosure, the amount of sFLT-1 measured in an individual may be used to diagnose myocardial infarction, based on the comparison of the amounts of soluble fms-like tyrosine kinase-1 (sFLT-1) or a variant thereof in a sample of said subject, to at least one reference amount. The method may comprise at least one of the following steps: a) determining the amount of soluble fms-like tyrosine kinase-1 (sFLT-1) or a variant thereof in a sample of said subject, b) comparing the amount of sFLT-1 or a variant thereof determined in step a) to at least one reference amount, and c) diagnosing myocardial infarction, in particular non ST elevated myocardial infarction based on the information obtained in step b), and based on the information obtained in a) and b). This also aides in allowing the individual to be observed for prolonged periods of time, such as 6 hours or more, even for more than 12 hours or 24 hours.

Accordingly, the present disclosure also relates to a method of diagnosing myocardial infarction, such as non ST elevated myocardial infarction, in a subject showing the signs and symptoms of acute coronary syndrome ACS but not fulfilling the diagnostic criteria for a myocardial infarction, comprising the steps of
  a) determining the amount of soluble fms-like tyrosine kinase-1 (sFLT-1) or a variant thereof in a sample of said subject,
  b) comparing the amount of sFLT-1 or a variant thereof as determined in step a) to at least one reference amount, and
  c) diagnosing myocardial infarction, in particular non ST elevated myocardial infarction based on the information obtained in step b), preferably based on the information obtained in a) and b).

Moreover, the present disclosure relates to a method for diagnosing myocardial infarction, such as non ST elevated myocardial infarction, in a subject showing signs and symptoms of acute coronary syndrome but not fulfilling the diagnostic criteria for a myocardial infarction, comprising
  a) comparing the amount of sFLT-1 or a variant thereof determined in a sample of said subject to at least one reference amount, and
  b) diagnosing myocardial infarction based on the information obtained in step a).

Moreover, the present disclosure relates to a method for diagnosing myocardial infarction, such as non ST elevated myocardial infarction, in a subject showing signs and symptoms of acute coronary syndrome but not fulfilling the diagnostic criteria for a myocardial infarction, comprising
  a) diagnosing myocardial infarction, in particular non ST elevated myocardial infarction, based on the comparison of the amount of sFLT-1 or a variant thereof determined in a sample of said subject to at least one reference amount.

Hepatocyte growth factor (HGF) was first identified in 1984 and 1985 and purified as a potent mitogen of primary cultured hepatocytes. HGF is single-chain precursor form, and further processing by serine proteases into the two-chain form is coupled to its activation. Serine proteases responsible for the activation of HGF include HGF activator or HGF converting enzyme and urokinase-type plasminogen activator (uPA). The receptor for HGF was identified as a c-met proto-oncogene product. The c-Met receptor is composed of a 50-kDa a-chain and 145-kDa h-chain. Binding of HGF to the c-Met receptor induces activation of tyrosine kinase, resulting in subsequent phosphorylation of C-terminally clustered tyrosine residues. HGF has an organotrophic role in the regeneration and protection of various organs, including the liver, lung, stomach, pancreas, heart, brain, and kidney. Hepatocyte growth factor regulates cell growth, cell motility, and morphogenesis by activating a tyrosine kinase signalling cascade after binding to the proto-oncogenic c-Met receptor. Hepatocyte growth factor is secreted by mesenchymal cells and acts as a multi-functional cytokine on cells of mainly epithelial origin. Its ability to stimulate mitogenesis, cell motility, and matrix invasion gives it a central role in angiogenesis, tumorogenesis, and tissue regeneration. It is secreted as a single inactive polypeptide and is cleaved by serine proteases into a 69-kDa alpha-chain and 34-kDa beta-chain. A disulfide bond between the alpha and beta chains produces the active, heterodimeric molecule. The protein belongs to the plasminogen subfamily of S1 peptidases but has no detectable protease activity. Alternative splicing of this gene produces multiple transcript variants encoding different isoforms. An amino acid sequence for mouse HGF is shown in Genebank accession number NP034557.2, GI: 46048249. An amino acid sequence for human HGF is shown in Genebank accession number NP000592.3 GI:33859835. As used herein, HGF in general refers to human HGF. Moreover, it is to be understood that a variant as referred to in accordance with the present disclosure comprises an amino acid sequence which differs due to at least one amino acid substitution, deletion and/or addition wherein the amino acid sequence of the variant is still, at least about 50%, 60%, 70%, 80%, 85%, 90%, 92%, 95%, 97%, 98%, or 99% identical with the amino sequence of the specific HGF. Variants may be allelic variants, splice variants or any other species specific homologs, paralogs, or orthologs. Moreover, the variants referred to herein include fragments of the specific HGF or the aforementioned types of variants as long as these fragments have the essential immunological and biological properties as referred to above. HGF variants have immunological properties (i.e. epitope composition) and/or biological properties comparable to those of human HGF. The variants are recognizable by the aforementioned means or ligands used for determination of the amount of the cardiac troponins. Such fragments may be, e.g., degradation products of HGF. Further included are variants which differ due to posttranslational modifications such as glycosylation, phosphorylation or myristylation. The biological property of HGF is the ability to bind to the proto-oncogenic c-Met receptor.

In further embodiments of the present disclosure, the amount of HGF measured in an individual may be used to diagnose myocardial infarction, based on the comparison of the amounts of hepatocyte growth factor (HGF) or a variant thereof in a sample of said subject, to at least one reference amount. The method may comprise at least one of the following steps: a) determining the amount of hepatocyte growth factor (HGF) or a variant thereof in a sample of said subject, b) comparing the amount of HGF or a variant thereof determined in step a) to at least one reference amount, and c) diagnosing myocardial infarction, in particular non ST elevated myocardial infarction based on the information obtained in step b), based on the information obtained in a) and b). This aides in allowing the individual to be observed for prolonged periods of time, such as more than 6 hours, more than 8 hours, and even more than 12 hours and more than 24 hours.

Accordingly, the present disclosure also relates to a method of diagnosing myocardial infarction, in particular non ST elevated myocardial infarction, in a subject showing the signs and symptoms of acute coronary syndrome ACS but not fulfilling the diagnostic criteria for a myocardial infarction, comprising the steps of
a) determining the amount of soluble HGF or a variant thereof in a sample of said subject, and
b) comparing the amount of HGF or a variant thereof as determined in step a) to at least one reference amount
c) diagnosing myocardial infarction, in particular non ST elevated myocardial infarction based on the information obtained in step b), or based on the information obtained in a) and b).

Moreover, the present disclosure relates to a method for diagnosing myocardial infarction, in particular non ST elevated myocardial infarction, in a subject showing signs and symptoms of acute coronary syndrome but not fulfilling the diagnostic criteria for a myocardial infarction, comprising
a) comparing the amount of HGF or a variant thereof determined in a sample of said subject to at least one reference amount, and
b) diagnosing myocardial infarction based on the information obtained in step a).

Moreover, the present disclosure relates to a method for diagnosing myocardial infarction, in particular non ST elevated myocardial infarction, in a subject showing signs and symptoms of acute coronary syndrome but not fulfilling the diagnostic criteria for a myocardial infarction, comprising
a) diagnosing myocardial infarction, in particular non ST elevated myocardial infarction, based on the comparison of the amount of HGF or a variant thereof determined in a sample of said subject to at least one reference amount.

The term "ANP-type peptides" comprises pre-proANP, proANP, NT-proANP, ANP variants thereof (see e.g. Bonow, 1996, Circulation 93: 1946-1950). The pre-pro peptide comprises a short signal peptide, which is enzymatically cleaved off to release the pro peptide. The pro peptide is further cleaved into an N-terminal pro peptide (NT-proANP) and the active hormone ANP with 28 amino acids. ANP has a vasodilatory effect and causes excretion of water and sodium via the urinary tract.

ANP has a shorter half-life than its inactive counterpart NT-proANP. ANP is produced and released exclusively from the atrium. The amount of ANP may therefore predominantly reflect atrial function. The term "variants" in this context relates to peptides substantially similar to ANP and NT-proANP. The term "substantially similar" is well understood by the person skilled in the art. In particular, a variant may be an isoform or allele which shows amino acid exchanges compared to the amino acid sequence of the most prevalent peptide isoform in the human population. Moreover, it is to be understood that a variant as referred to in accordance with the present disclosure shall have an amino acid sequence which differs due to at least one amino acid substitution, deletion and/or addition wherein the amino acid sequence of the variant is still, at least 50%, 60%, 70%, 80%, 85%, 90%, 92%, 95%, 97%, 98%, or 99% identical with the amino sequence of ANP or NT-proANP. Variants may be allelic variants, splice variants or any other species specific homologs, paralogs, or orthologs. Substantially similar are also proteolytic degradation products which are still recognized by the diagnostic means or by ligands directed against the respective full-length peptide. as long as these fragments have the essential immunological and biological properties as referred to above. The ANP-type peptide variants have immunological properties (i.e. epitope composition) and biological properties comparable to those of the respective human ANP-type peptide. Thus, the variants shall be recognizable by the aforementioned means or ligands used for determination of the amount of the ANP-type peptide. Such fragments may be, e.g., degradation products of NT-proANP. Further included are variants which differ due to posttranslational modifications such as glycosylation, phosphorylation or myristylation. The biological property of ANP is the vasodilatory ability and/or the ability of sodium and water excretion.

The term "variant" also relates to a post-translationally modified peptide such as glycosylated peptide. A "variant" is also a peptide which has been modified after collection of the sample, for example by covalent or non-covalent attachment of a label, particularly a radioactive or fluorescent label, to the peptide. Measuring the amount of a peptide modified after collection of the sample is understood as measuring the amount of the originally non-modified peptide.

In the context of the present disclosure, the ANP-type peptide may comprise NT-proANP.

The term "sample" refers to a sample of a body fluid, to a sample of separated cells or to a sample from a tissue or an organ. Samples of body fluids can be obtained by well-known techniques and include, for example, samples of blood, plasma, serum, or urine. Tissue or organ samples may be obtained from any tissue or organ by biopsy, for example. Separated cells may be obtained from the body fluids or the tissues or organs by separating techniques such as centrifugation or cell sorting. Cell-, tissue- or organ samples may be obtained from those cells, tissues or organs which express or produce the peptides referred to herein. The term "sample" may refer to a plasma or serum sample, for example.

In the present disclosure, the sample may be obtained at an appropriate time-point which is known by the skilled person. It has to be taken into consideration that the subject under examination suffers from an acute pathophysiological state (ACS), requiring rapid diagnosis and a rapid decision on an appropriate treatment. In some cases, the sample may be obtained from a subject according the present disclosure shortly, e.g. after about 1 h, not more than about 2 hours, not more than about 3 hours, not more than about 4 hours, not more than about 5 hours, or not more than about 6 hours after the onset of symptoms of acute coronary syndrome. The sample may be taken immediately (i.e. within a few minutes, i.e. within about 5, about 10, about 15, about 30, about 45, or about 1 h) after presentation of the subject to the physician, for example.

In case the amounts of sFLT-1 and/or, optionally, HGF and/or optionally a ANP type peptide are determined repeatedly, such as at least twice, to monitor the severity of the ischemia, the second and each further sample will be taken in an interval which aides in an effective monitoring of the ischemic state. In general, the interval between each sample is about 15 minutes, about 30 minutes, about 45 minutes, about 1 hour, about 90 minutes, about 2 hours, about 3, 4, 5, or 6 hours. For example, the initial samples may be taken about 1 hour after the onset of signs and/or symptoms of acute coronary syndrome or immediately after the presentation of the subject to the physician, and each further sample may be taken about 1 hour after the initial samples. The number of samples taken may also depend on the evaluation of the ischemia.

Determining the amount of a cardiac troponin, such as troponin T, or the amount of sFLT-1, or the amount of HGF, or any other peptide or polypeptide or protein referred to in this specification relates to measuring the amount or concentration, for example semi-quantitatively or quantitatively. The terms polypeptide and protein are used interchangeable throughout this application. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present disclosure, determining the amount of a peptide or polypeptide can be achieved by all known means for determining the amount of a peptide in a sample. Said means comprise immunoassay devices and methods which may utilize labelled molecules in various sandwich, competition, or other assay formats. Said assays may develop a signal which is indicative for the presence or absence of the peptide or polypeptide. Moreover, the signal strength may, be correlatable directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods may comprise biosensors, optical devices coupled to immunoassays, biochips, analytical devices such as mass-spectrometers, NMR-analyzers, or chromatography devices, for example. Further, methods may include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Determining the amount of a peptide or polypeptide may comprise the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample may be added to a cell culture and an internal or external cellular response may be measured. The cellular response may include the measurable expression of a reporter gene or the secretion of a substance, e.g., a peptide, polypeptide, or a small molecule. The expression or substance may generate an intensity signal which correlates to the amount of the peptide or polypeptide.

Also, determining the amount of a peptide or polypeptide may comprise the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may comprise the steps of (a) contacting the peptide with a specific ligand, (b) (optionally) removing non-bound ligand, (c) measuring the amount of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. The ligand or agent binds specifically to the peptide or polypeptide. Specific binding according to the present disclosure means that the ligand or agent should not bind substantially to ("cross-react" with) another peptide, polypeptide or substance present in the sample to be analyzed. The specifically bound peptide or polypeptide may bind with approximately at least 3 times higher, at least 10 times higher and in some cases at least 50 times higher affinity than any other relevant peptide or polypeptide. Non-specific binding may also be tolerable, if it can still be distinguished and measured unequivocally, e.g. according to its size on a Western Blot, or by its relatively higher abundance in the sample. Binding of the ligand can be measured by any method known in the art. Said method may be semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, the amount of substrate may be saturating. The substrate may also be labelled with a detectable label prior to the reaction. The sample may be contacted with the substrate for an adequate period of time. An adequate period of time refers to the time necessary for a detectable, and generally measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.).

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a coloured reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P, and the like. A radioactive label can be detected by any method known and appropriate, e.g. a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labelling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand may be chosen from the group consisting of nucleic acids, peptides, polypeptides, antibodies and aptamers, and may be present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (see, for example, Nolan 2002, Trends Biotechnol. 20(1):9-12). In such suspension arrays, the carrier, e.g. a microbead or microsphere, is present in suspension. The array consists of different microbeads or microspheres, possibly labelled, carrying different ligands. Methods of producing such arrays, for example based on solid-phase chemistry and photo-labile protective groups, are generally known (see, U.S. Pat. No. 5,744,305).

According to embodiments of the instant disclosure, the amount of sFLT-1 and the amount of HGF (if HGF is measured) and the amount of the ANP-type peptides and, as the case may be, the amounts of other peptides measured in the context of the present disclosure may be determined in a blood sample, (or for example, a serum or plasma sample), obtained from a subject as defined in the present disclosure. Such a determination may be done by ELISA. Such a determination by ELISA can be done, e.g., by using the Quantikine Human HGF Immunoassay, R&D Systems, Inc., Minneapolis, Minn., USA, and/or the Quantikine Human Soluble VEGF R1/Flt-1 Immunoassay (for sFLT-1), R&D Systems, Inc., Minneapolis, Minn., USA, and the NT-proANP immunoassay by Biomedica Medizinprodukte, Vienna, Austria. As the case may be, the respective amounts of sFLT-1 and/or of HGF as specified elsewhere in this application can be determined by using the HBT ELISA Test Kit for human heart type fatty acid binding protein (HyCult Biotechnology, Uden, The Netherlands) for the determination of the amount of H-FABP and by using the Tina-Quant® Myoglobin Test System (Roche Diagnostics) for the determination of the amount of myoglobin, respectively.

The term "amount" as used herein encompasses any of the absolute amount (e.g., of sFLT-1 or HGF), the relative amount or concentration (e.g. of sFLT-1 or HGF) as well as any value or parameter which correlates thereto. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., expression amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide, polypeptide, protein comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present disclosure may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount(s) determined in step a) to suitable reference amount(s), it is possible to diagnose MI in said subject. It is to be understood that an amount of sFLT-1 as determined in step (a) of the methods of the presents disclosure is compared in step (b) to a reference amount for sFLT-1 as specified elsewhere in this application and that an amount of HGF is compared to a reference amount for HGF.

Accordingly, the term "reference amount" as used herein may refer to either an amount which allows determining the ischemic state (which may also be referred to as "degree of ischemia" in the context of the present disclosure) in a subject showing the signs and symptoms of acute coronary syndrome and has a cardiac Troponin amount which is lower than the amount that is considered as being indicative for a myocardial infarction (thus in a subject as defined in the present disclosure). The comparison with reference amounts permits to diagnose if the ischemia will lead to a cardiac dysfunction/ cardiac injury. The onset of symptoms of ACS has occurred recently. Recent occurrence in this context means that the onset has occurred, preferably, within a 6 hour period, more preferably within a 4 hour period, and most preferably within a 2 hour period before the sample was obtained from said subject. Reference amounts for the severity of the degree of ischemia may be derived from subjects as defined in the present disclosure diagnosed as having the symptoms of ACS having shown up within a 6 hour period, within a 4 hour period and in some cases within a 2 hour period before the sample was obtained, and where the subject's outcome was determined, namely occurrence of MI, in particular NSTEMI, UAP, myocardial stunning, circulatory dysfunction, or CAD without signs of ACS.

The term "reference amounts" as used herein in this embodiment of the disclosure refers to amounts of the polypeptides which allow diagnosing the ischemic state in an individual as being that of a physiologically healthy subject, or a subject having an ischemic state leading to a reversible cardiac dysfunction or to non-reversible cardiac injury. Therefore, the reference amounts will in general be derived from a subject known to be a physiologically healthy subject, or a subject having an ischemic state leading to a reversible cardiac dysfunction or to non-reversible cardiac injury.

In all embodiments of the present disclosure, the amounts/ amounts of the respective markers used therein (a cardiac troponin, in particular troponin T; sFLT-1; HGF; and, in some embodiments, NT-proANP) indicating the ischemic state in an individual, are determined by methods known to the person skilled in the art.

According to the subject disclosure, determining the respective amounts/amounts or amount ratios allowing to establish the desired diagnosis in accordance with the respective embodiment of the present disclosure, ("threshold", "reference amount"), the amount(s)/amount(s) or amount ratios of the respective peptide or peptides are determined in appropriate patient groups. According to the diagnosis to be established, the patient group may, for example, comprise only healthy individuals, or may comprise healthy individuals and individuals suffering from the pathophysiological state which is to be determined, or may comprise only individuals suffering from the pathophysiological state which is to be determined, or may comprise individuals suffering from the various pathophysiological states to be distinguished, by the respective marker(s) using validated analytical methods. The results which are obtained are collected and analyzed by statistical methods known to the person skilled in the art. The obtained threshold values are then established in accordance with the desired probability of suffering from the disease and linked to the particular threshold value. For example, it may be useful to choose the median value, the $60^{th}$, $70^{th}$, $80^{th}$, $90^{th}$, $95^{th}$ or even the $99^{th}$ percentile of the healthy and/or non-healthy patient collective, in order to establish the threshold value(s), reference value(s) or amount ratios.

A reference value of a diagnostic marker can be established, and the amount of the marker in a patient sample can simply be compared to the reference value. The sensitivity and specificity of a diagnostic and/or prognostic test depends on more than just the analytical "quality" of the test-they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker of the disclosure, a distribution of marker amounts for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al, Radiology 143: 29-36 (1982).

In certain embodiments, markers and/or marker panels are selected to exhibit at least about 70% sensitivity, at least about 80% sensitivity, at least about 85% sensitivity, at least about 90% sensitivity, and at least about 95% sensitivity, combined with at least about 70% specificity, at least about 80% specificity, at least about 85% specificity, at least about 90% specificity, and at least about 95% specificity. According to some embodiments, both the sensitivity and specificity are at least about 75%, at least about 80%, at least about 85%, at least about 90%, and at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In some embodiments, markers and/or marker panels may be selected to exhibit a positive or negative likelihood ratio of at least about 1.5 or more or about 0.67 or less, at least about 2 or more or about 0.5 or less, at least about 5 or more or about 0.2 or less, at least about 10 or more or about 0.1 or less, and at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain embodiments, markers and/or marker panels may be selected to exhibit an odds ratio of at least about 2 or more or about 0.5 or less, at least about 3 or more or about 0.33 or less, at least about 4 or more or about 0.25 or less, and even at least about 5 or more or about 0.2 or less, and in some cases at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain embodiments, markers and/or marker panels may be selected to exhibit a hazard ratio of at least about 1.1 or more or about 0.91 or less, for example at least about 1.25 or more or about 0.8 or less, or even at least about 1.5 or more or about 0.67 or less, and some embodiments may be at least about 2 or more or about 0.5 or less, and even at least about 2.5 or more or about 0.4 or less. The term "about" in this context refers to +/−5% of a given measurement.

While exemplary panels are described herein, one or more markers may be replaced, added, or subtracted from these exemplary panels while still providing clinically useful results. Panels may comprise both specific markers of a disease (e.g., markers that are increased or decreased in bacterial infection, but not in other disease states) and/or non-specific markers (e.g., markers that are increased or decreased due to inflammation, regardless of the cause; markers that are increased or decreased due to changes in hemostasis, regardless of the cause, etc.). While certain markers may not individually be definitive in the methods described herein, a particular "fingerprint" pattern of changes may, in effect, act as a specific indicator of disease state. As discussed above, that pattern of changes may be obtained from a single sample, or may optionally consider temporal changes in one or more members of the panel (or temporal changes in a panel response value).

In order to test if a chosen reference value yields a sufficiently safe diagnosis of patients suffering from the disease of interest, one may for example determine the efficiency (E) of the methods of the disclosure for a given reference value using the following formula: $E=(TP/TO)\times 100$; wherein TP=true positives and TO=total number of tests=TP+FP+FN+TN, wherein FP=false positives; FN=false negatives and TN=true negatives. E has the following range of values: $0<E<100$). A tested reference value may yield a sufficiently safe diagnosis provided the value of E is at least about 50, and in some cases at least about 60, in some embodiments at least about 70, in some other cases at least about 80, in some cases at least about 90, and in some embodiments at least about 95 or at least about 98.

The diagnosis if individuals are healthy or suffer from a certain pathophysiological state may be made by established methods known to the person skilled in the art. The methods may differ in respect to the individual pathophysiological state.

The algorithms to establish the desired diagnosis are laid out in the present application, in the passages referring to the respective embodiment, to which reference is made.

Accordingly, the present disclosure also comprises a method of determining the threshold amount indicative for a physiological and/or a pathological state and/or a certain pathological state, comprising the steps of determining in appropriate patient groups the amounts of the appropriate marker(s), collecting the data and analyzing the data by statistical methods and establishing the threshold values.

The term "about" as used herein refers to +/−20%, and ins some embodiments may refer to +/−10% or even+/−5% of a given measurement or value.

Reference amounts for sFLT-1 indicating ischemic states as defined in the present disclosure (threshold amounts) are the following: about 92 pg/ml, and in some embodiments about 109 pg/ml. Amounts of sFLT-1 below the above-cited values are indicative for a non-ischemic state not associated with or leading to reversible cardiac dysfunction or non-reversible cardiac injury. Amounts of sFLT-1 equal to or larger than the above-quoted reference amounts are indicative for an ischemic state associated with or leading to reversible cardiac dysfunction or non-reversible cardiac injury.

A reference amount for HGF for ischemic states as defined in the present disclosure (threshold amounts) are the following: about 0.62 pg/ml, and in some embodiments about 0.73 pg/ml. Amounts of HGF below the above-cited values are indicative for non-ischemic state not associated with or leading to reversible cardiac dysfunction or non-reversible cardiac injury. Amounts of HGF equal to or larger than the above-quoted reference amounts are indicative for an ischemic state associated with or leading to reversible cardiac dysfunction or non-reversible cardiac injury.

In some embodiments, the determined sFLT-1 and, optionally, the HGF values do not indicate an ischemic state, the individual does not require any further examination in respect to cardiac diseases. In general, such individual can be released home.

In case an ischemic state is diagnosed, the respective individual may require further examination in respect to cardiac or cardiovascular diseases. An exemplary embodiment according to the present disclosure comprises steps of further diagnosing the individual in whom the amounts of sFLT-1 and/or HGF have been determined. Appropriate further diagnostic methods in the context of the present disclosure include stress testing of various kinds, e.g. stress exercise ECG, stress exercise echocardiography, stress exercise computer tomography, stress exercise thallium scan; and angiography (invasive or virtual, e.g. by spiral computer tomography).

The reference amounts for NT-proANP for a circulatory impairment as defined in the present disclosure, (threshold amounts) comprise the following: about 1320 pg/ml and in some embodiments about 1674 pg/ml. Amounts of NT-proANP equal to or larger than the above-cited values are indicative for a circulatory impairment.

The values for HGF and NT-proANP may change due to the occurrence of chronic diseases in an individual, e.g. heart failure, renal impairment or failure and—in case of HGF—acute or chronic liver disease. In case of a chronic disease, the values cited above may be significantly higher (e.g. 2 5, 7, 8 or 10 times higher) than the values cited beforehand which are applicable for individuals not having a chronic disease, in particular not a chronic heart disease, further to the acute coronary syndrome.

The phrase "at least one reference amount" means one or more than one reference amount, e.g. two reference amounts.

In an exemplary embodiment of the present disclosure, the determination of the above-cited markers is carried out in intervals, in order to determine the evaluation of the marker amount. This may be helpful in the assessment if an acute event occurs/has occurred or not.

An acute event is assumed if the determined amount of at least one of the markers sFLT-1, HGF and/or NT-proANP is larger than the reference amounts cited beforehand. In some embodiments, the deviation is, at least about 20%, or at least about 30%, or at least about 50%, or at least about 100%, or at least about 200%, or even at least about 500%, and in some cases at least about 1000%.

The time interval in between two determinations of a given marker (or the markers) is at least about 15 minutes, at least about 30 minutes, at least about 45 minutes, at least about 1 hour, at least about 90 minutes, at least about 2 hours, at least about 3, at least about 4, at least about 5, or at least about 6 hours. The person skilled in the art is aware that the time interval and the deviation may vary, in accordance with the state of the individual, the trend of the amount of the respective marker to change (i.e. the development of ischemia and/or circulatory impairment), etc.

Another embodiment of the present disclosure comprises the determination of H-FABP and/or myoglobin, after determining a cardiac troponin and/or measuring an ECG, and before determining the amounts of sFLT-1 and, optionally, HGF in steps a) and b) of the method of the present disclosure, in order to determine if the subject has suffered from a myocardial infarction, in particular a NSTEMI.

An amount of myoglobin and, optionally H-FABP, in a subject as defined in the present disclosure of larger than the reference amount for ruling in the occurrence of MI shall be indicative for a recent occurrence of MI in said subject. An amount of myoglobin and, optionally, H-FABP in a subject as defined in the present disclosure lower than the reference amount for ruling out the occurrence of MI shall be an indicator that a MI infarction has not occurred recently, thus said subject might suffer from UAP. It is to be understood in the context of the present disclosure that subjects as defined in the present disclosure whose myoglobin amount is between the above mentioned reference amounts (the reference amount for ruling in the recent occurrence of MI and the reference amount for ruling out the recent occurrence of MI) may be required to be diagnosed again. This may be also done for subjects in which both the amount of myoglobin and H-FABP are determined, wherein both amounts do not correspond, e.g. one amount is larger (or lower) than the respective reference amount, whereas the other amount is not larger (or lower) than the respective reference amount. A myoglobin amount in a subject as defined in the present disclosure of larger than 77 ng/ml indicates a recent occurrence of MI (rule in), whereas an amount of less than 55 ng/ml indicates that a MI did not occur recently (rule out). Moreover, the sensitivity and specificity of the diagnosis based on the determination of myoglobin in a sample of a subject as defined in the present disclosure is even more increased when in addition to the amount of myoglobin, the amount of H-FABP is determined in a sample of said subject and compared to at least one reference amount for H-FABP. An H-FABP amount in a subject as defined in the present disclosure of larger than 5700 pg/ml indicates a recent occurrence of MI (rule in), whereas an amount of less than 2500 pg/ml indicates that a MI did not occur recently (rule out).

Myoglobin is a cytoplasmic hemoprotein consisting of a single polypeptide chain of 154 amino acids and is almost exclusively expressed solely in cardiac myocytes and oxidative skeletal muscle fibers. Like hemoglobin, myoglobin reversibly binds oxygen and thus may facilitate oxygen transport from red blood cells to mitochondria during periods of increased metabolic activity or serve as an oxygene reservoir during hypoxic or anoxic conditions (see, Ordway G. and Garry D. J., Myoglobin: an essential hemoprotein in striated muscle. 2004. Journal of Experimental Biology 207, 3441-3446 (2004)).

Heart-type fatty acid binding protein, herein also referred to as H-FABP or heart fatty acid binding protein, is a small cytosolic protein that functions as the principal transporter of long-chain fatty acids in the cardiomyocyte, from the cell membrane to their intracellular sites of metabolism in the mitochondria, where they enter the citric acid cycle. H-FABP is present in the myocardium and it is generally thought to be released rapidly into the circulation in response to myocardial injury. Several studies show that H-FABP is an early biochemical marker of myocardial infarction (for example, Okamoto et al., Clin Chem Lab Med 38(3):231-8 (2000) Human heart-type cytoplasmic fatty acid-binding protein (H-FABP) for the diagnosis of acute myocardial infarction. Clinical evaluation of H-FABP in comparison with myoglobin and creatine kinase isoenzyme MB; O'Donoghue et al., Circulation, 114; 550-557 (2006) Prognostic Utility of Heart-Type Fatty Acid Binding Protein in patients with acute coronary syndrome or Ruzgar et al., Heart Vessels, 21; 209-314 (2006) The use of human heart-type fatty acid-binding protein as an early diagnostic marker of myocardial necrosis in patients with acute coronary syndrome, and its comparison with troponinT and its creatine kinase-myocardial band).

Myoglobin and H-FABP as used herein encompasses also variants of myoglobin and H-FABP polypeptides, respectively. Such variants have at least the same essential biological and immunological properties as the specific myoglobin and H-FABP polypeptides. In particular, they share the same essential biological and immunological properties if they are detectable by the same specific assays referred to in this specification, e.g., by ELISA assays using polyclonal or monoclonal antibodies specifically recognizing the said myoglobin and H-FABP polypeptides, respectively. Moreover, it is to be understood that a variant as referred to in accordance with the present disclosure shall have an amino acid sequence which differs due to at least one amino acid substitution, deletion and/or addition wherein the amino acid sequence of the variant is still, at least 50%, 60%, 70%, 80%, 85%, 90%, 92%, 95%, 97%, 98%, or 99% identical with the amino sequence of the specific H-FABP and myoglobin polypeptides, respectively. The degree of identity between two amino acid sequences can be determined by algorithms well known in the art. The degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT may be employed to determine their optimal alignment and, thus, the degree of identity. The default values of 5.00 for gap weight and 0.30 for gap weight length are used. Variants referred to above may be allelic variants or any other species specific homologs, paralogs, or orthologs. Moreover, the variants referred to herein include fragments of the specific myoglobin and H-FABP polypeptides or the aforementioned types of variants as long as these fragments have the essential immunological and biological properties as referred to above. Such fragments may be, e.g., degradation products of the myoglobin and H-FABP polypeptides. Further included are variants which differ due to posttranslational modifications such as phosphorylation or myristylation. The biological properties of myoglobin comprise the ability to reversibly bind oxygen. The biological property of H-FABP comprises the transport of long-chain fatty acids from the cell membrane to their intracellular sites of metabolism in the mitochondria, where they enter the citric acid cycle.

It is to be understood that according to the method of the present disclosure described herein above and below, the antibodies for sFLT-1 and, in some embodiments, HGF or means for the determination thereof can be used for the manufacture of a diagnostic composition for diagnosing ischemia and the course of the severity of ischemia in a subject showing the signs and symptoms of acute coronary syndrome and having a cardiac Troponin amount which is lower than the amount considered as being indicative for a myocardial infarction.

The present disclosure also relates to a method for stratifying or assessing the risk of a subject showing the signs and symptoms of acute coronary syndrome ACS but not fulfilling the diagnostic criteria for a myocardial infarction, to suffer from a myocardial infarction, based on the comparison of the amounts of soluble fms-like tyrosine kinase-1 (sFLT-1) or a variant thereof in a sample of said subject, to at least one reference amount. The method may comprise at least one of the following steps: a) determining the amount of sFLT-1 or a variant thereof in a sample of said subject, b) comparing the amount of sFLT-1 or a variant thereof determined in step a) to at least one reference amount, c) diagnosing the ischemic state based on the information obtained in step b, and/or in steps a) and b), d) assessing the risk to suffer from a myocardial infarction, based on the information obtained in c).

The present disclosure also relates to a method for stratifying or assessing the risk of a subject showing the signs and symptoms of acute coronary syndrome ACS but not fulfilling the diagnostic criteria for a myocardial infarction, to suffer from a myocardial infarction, comprising
  a) determining the amount of sFLT-1 or a variant thereof in a sample of said subject, and
  b) comparing the amount of sFLT-1 or a variant thereof determined in step a) to at least one reference amount,
  c) diagnosing the ischemic state based on the information obtained in step b, preferably in steps a) and b), and
  d) assessing the risk to suffer from a myocardial infarction, based on the information obtained in c).

The present disclosure also relates to a method for identifying a subject susceptible to cardiac intervention, showing the signs and symptoms of acute coronary syndrome ACS but not fulfilling the diagnostic criteria for a myocardial infarction, based on the comparison of the amounts of soluble fms-like tyrosine kinase-1 (sFLT-1) or a variant thereof in a sample of said subject, to at least one reference amount. The method may comprise at least one of the following steps: a) determining the amount of sFLT-1 or a variant thereof in a sample of said subject, b) comparing the amount of sFLT-1 or a variant thereof determined in step a) to at least one reference amount, c) diagnosing the ischemic state based on the information obtained in step b and/or in steps a) and b), d) assessing the risk to suffer from a myocardial infarction, based on the information obtained in c).

Accordingly, the present disclosure further relates to a method for identifying a subject susceptible to cardiac intervention, whereby the subject shows signs and symptoms of acute coronary syndrome but not fulfilling the diagnostic criteria for a myocardial infarction, comprising
  a) determining the amount of sFLT-1 or a variant thereof in a sample of said subject, and
  b) comparing the amount of sFLT-1 or a variant thereof determined in step a) to at least one reference amount,
  c) diagnosing the ischemic state based on the information obtained in step b), preferably in steps a) and b), and d) identifying the subject, based on the information obtained in c).

Moreover, the present disclosure also relates to a method of recommending or deciding on a possible cardiac intervention or initiating a possible cardiac intervention in a subject, showing the signs and symptoms of acute coronary syndrome ACS but not fulfilling the diagnostic criteria for a myocardial infarction, based on the comparison of the amounts of soluble fms-like tyrosine kinase-1 (sFLT-1) or a variant thereof in a sample of said subject, to at least one reference amount. The method may comprise at least one of the following steps: a) determining the amount of sFLT-1 or a variant thereof in a sample of said subject, b) comparing the amount of sFLT-1 or a variant thereof determined in step a) to at least one reference amount, c) recommending or deciding on the initiation of a cardiac intervention, initiating the cardiac intervention or refraining from the cardiac intervention, based on the information obtained in step c).

Accordingly, the present disclosure relates to a method of recommending or deciding on a possible cardiac intervention or initiating a possible cardiac intervention in a subject showing signs and symptoms of acute coronary syndrome but not fulfilling the diagnostic criteria for a myocardial infarction, comprising
- a) determining the amount of sFLT-1 or a variant thereof in a sample of said subject, and
- b) comparing the amount of sFLT-1 or a variant thereof determined in step a) to at least one reference amount,
- c) diagnosing the ischemic state based on the information obtained in step b), preferably in steps a) and b), and
- d) recommending or deciding on the initiation of a cardiac intervention, initiating the cardiac intervention or refraining from the cardiac intervention, based on the information obtained in step c).

In all embodiments cited beforehand, including methods for stratifying or assessing the risk of a subject to suffer from a myocardial infarction, a method for identifying a subject susceptible to cardiac intervention, and a method of recommending or deciding on a possible cardiac intervention or initiating a possible cardiac intervention in a subject, with the subject showing signs and symptoms of acute coronary syndrome but not fulfilling the diagnostic criteria for a myocardial infarction, each method may also be carried out using the following steps:
- a) diagnosing the ischemic state based on determining the amount of sFLT-1 or a variant thereof in a sample of said subject, and comparing the amount of sFLT-1 or a variant thereof to at least one reference amount; and
- b) based on the information obtained in a),
- bi) assessing the risk of the subject to suffer from a myocardial infarction; and/or
- bii) identifying a subject susceptible to cardiac intervention; and/or
- biii) recommending or deciding on a possible cardiac intervention or initiating a possible cardiac intervention in a subject Moreover, the present disclosure, in all embodiments cited beforehand, including methods for stratifying or assessing the risk of a subject to suffer from a myocardial infarction, a method for identifying a subject susceptible to cardiac intervention, and a method of recommending or deciding on a possible cardiac intervention or initiating a possible cardiac intervention in a subject, with the subject showing signs and symptoms of acute coronary syndrome but not fulfilling the diagnostic criteria for a myocardial infarction, comprises an embodiment for each method using the following steps:
- ai) assessing the risk of the subject to suffer from a myocardial infarction; and/or
- aii) identifying a subject susceptible to cardiac intervention; and/or
- aiii) recommending or deciding on a possible cardiac intervention or initiating a possible cardiac intervention in a subject;
- wherein all steps ai), aii) and/or aiii) are based on diagnosing the ischemic state in the subject by determining the amount of sFLT-1 or a variant thereof in a sample of said subject, and comparing the amount of sFLT-1 or a variant thereof to at least one reference amount.

In an embodiment of the aforementioned method of the present disclosure, additionally the amount of hepatocyte growth factor (HGF) or a variant thereof is determined in an additional step aa) in a sample of said subject and compared to at least one reference amount for HGF in step bb). Accordingly, in step c), the ischemic state is diagnosed based on the determined amounts of sFLT-1 or a variant thereof and HGF or a variant thereof and the comparison of the amount of sFLT-1 to at least one reference amount for sFLT-1 and the comparison of the amount of HGF to at least one reference amount for HGF. Preferably, first the amount of sFLT-1 and then the amount of HGF is determined, however is also contemplated that the amounts of sFLT-1 and HGF are determined in any order, i.e. simultaneously, or first sFLT-1 and then HGF, or first HGF and then sFLT-1.

In a further embodiment of the present disclosure, the amount of hepatocyte growth factor (HGF) or a variant thereof is determined in place of sFLT-1 in all embodiments cited beforehand, i.e. a method for stratifying or assessing the risk of a subject to suffer from a myocardial infarction, a method for identifying a subject susceptible to cardiac intervention, and a method of recommending or deciding on a possible cardiac intervention or initiating a possible cardiac intervention in a subject, with the subject showing signs and symptoms of acute coronary syndrome but not fulfilling the diagnostic criteria for a myocardial infarction. In an embodiment of this method of the present disclosure, additionally the amount of sFLT-1 or a variant thereof is determined in an additional step in a sample of said subject and compared to at least one reference amount for sFLT-1, in order to diagnose the ischemic state.

In some embodiments, the amounts of a cardiac troponin are determined simultaneously with the determination of sFLT-1 and/or the determination of HGF; the determination of the amounts of a cardiac troponin may also precede the determination of sFLT-1 and/or the determination of HGF. The ischemic state of the individual, therefore, may be determined simultaneously with or after troponin determination, by determining the amounts of sFLT-1 and/or HGF or, optionally, the further marker. Accordingly, if the cardiac troponin amount is determined prior to the determination of sFLT-1 and/or HGF, the determination of the amounts of sFLT-1 and/or HGF may be deferred until the amount of the cardiac troponin is known, and only in case the troponin amount is lower than the amount which is generally recognized in the art as being indicative for a myocardial infarction MI, in particular for a NSTEMI, the amount of sFLT-1 and/or HGF will be determined. The amount of the cardiac troponin may even be zero, i.e. not detectable with the tests presently available.

In some further embodiments, an ECG of the respective subject is determined simultaneously with the determination of sFLT-1 and/or the determination of HGF; measuring the ECG may also precede the determination of sFLT-1 and/or the determination of HGF. The ischemic state of the individual, therefore, may be determined simultaneously with or after measuring an ECG, by determining the amounts of sFLT-1 and, optionally, HGF. Accordingly, if the ECG measurement is carried out prior to the determination of sFLT-1 and/or HGF, the determination of the amounts of sFLT-1 and/or HGF may be deferred until the ECG is recorded. In case the subject's ECG does not show a ST elevation, the amount of sFLT-1 and/or HGF may be determined. In case the ECG shows a ST elevation, the subject may be considered to have suffered from a STEMI.

The above-mentioned embodiments of the present disclosure can be carried out such that only the level of a cardiac troponin is determined or an ECG is measured; or the method of the present disclosure includes both the determination of the level of a cardiac troponin and measuring and ECG.

The reference amounts of sFLT-1 and HGF are those cited beforehand to indicate an ischemic state in an individual.

Reference amounts for sFLT-1 indicating ischemic states as defined in the present disclosure (threshold amounts) are the following: about 92 pg/ml and in some cases more preferably about 109 pg/ml. Amounts of sFLT-1 below the above-cited values are indicative for a non-ischemic state not associated with or leading to reversible cardiac dysfunction or non-reversible cardiac injury. Amounts of sFLT-1 equal to or larger than the above-quoted reference amounts are indicative for an ischemic state associated with or leading to reversible cardiac dysfunction or non-reversible cardiac injury.

A reference amount for HGF for ischemic states as defined in the present disclosure (threshold amounts) are the following: about 0.62 pg/ml and in some cases more preferably about 0.73 pg/ml. Amounts of HGF below the above-cited values are indicative for non-ischemic state not associated with or leading to reversible cardiac dysfunction or non-reversible cardiac injury. Amounts of HGF equal to or larger than the above-quoted reference amounts are indicative for an ischemic state associated with or leading to reversible cardiac dysfunction or non-reversible cardiac injury.

In case the sFLT-1 and, optionally, HGF values do not indicate an ischemic state, the individual may not require further examination in respect to cardiac diseases and may be released home.

In case an ischemic disease is diagnosed by the amounts of sFLT-1 and optionally HGF, the respective individual, in some embodiments of the present disclosure, receives a treatment regimen as specified below, also referred to as "cardiac intervention".

In cases in which an ischemic disease is diagnosed by the amounts of sFLT-1 and optionally HGF, the respective individual may require further examination in respect to cardiac or cardiovascular diseases. In some embodiments, these further diagnostic methods in the context of the present disclosure may include stress testing of various kinds, such as stress exercise, stress exercise echocardiography, stress exercise computer tomography, stress exercise thallium scan; and angiography (invasive or virtual, e.g. by spiral computer tomography). Depending on the results of the further examination, the respective individual may receive a treatment regimen as specified below, also referred to as "cardiac intervention".

In a further embodiment of the present disclosure, the amount of NT-proANP is determined, in order to diagnose a possible circulatory impairment of the subject.

The reference amounts for the ANP type peptide, in particular NT-proANP, are those cited beforehand in connection with circulatory impairment Reference amounts for NT-proANP for circulatory impairment as defined in the present disclosure, (threshold amounts) are the following: about 1320 pg/ml and in somce cases more preferably about 1674 pg/ml. Amounts of NT-proANP equal to or larger than the above-cited values are indicative for a circulatory impairment.

Another embodiment of the present disclosure comprises the determination of H-FABP and/or myoglobin, after determining a cardiac troponin and/or measuring an ECG, and before determining the levels of sFLT-1 and, optionally, HGF in steps a) and b) of the method of the present disclosure, in order to determine if the subject has already suffered from a myocardial infarction, in particular a NSTEMI.

According to some embodiments of the instant disclosure, an amount of myoglobin and, optionally H-FABP, in a subject as defined in the present disclosure of larger than the reference amount for ruling in the occurrence of MI is indicative for a recent occurrence of MI in said subject. In some embodiments, an amount of myoglobin and, optionally, H-FABP in a subject as defined in the present disclosure lower than the reference amount for ruling out the occurrence of MI is an indicator that a MI infarction has not occurred recently, thus said subject might suffer from UAP. It is to be understood in the context of the present disclosure that subjects as defined in the present disclosure whose myoglobin amount is between the above mentioned reference amounts (the reference amount for ruling in the recent occurrence of MI and the reference amount for ruling out the recent occurrence of MI) may be required to be diagnosed again. For example, this may be also done for subjects in which both the amount of myoglobin and H-FABP are determined, wherein both amounts do not correspond, e.g. one amount is larger (or lower) than the respective reference amount, whereas the other amount is not larger (or lower) than the respective reference amount.

The methods disclosed herein provide for a risk/success stratification which can be easily performed before subjecting a patient to a cardiac intervention. In case the patient turns out to be not susceptible for a cardiac intervention, said dangerous, time and/or cost intensive therapy can be avoided. Thus, besides preventing a subject from the adverse and severe side effects accompanying a cardiac intervention, the method of the present disclosure may be beneficial for the health system in that resources will be saved.

It is to be understood in the context of the aforementioned method of the present disclosure that a subject diagnosed to not have suffered from MI, but having an ischemic state or a development of its ischemic state which is supposed to result in reversible cardiac dysfunction or non-reversible cardiac injury, is susceptible to cardiac intervention.

The term "identifying" as used herein means assessing whether a subject will be susceptible for a cardiac intervention or not. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant may be determined using one or more of various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Confidence intervals may be at least 90%, at least 95%, at least 97%, at least 98% or at least 99%. The p-values may be 0.1, 0.05, 0.01, 0.005, or 0.0001. According to the instant disclosure, at least 60%, at least 70%, at least 80% or at least 90% of the subjects of a population can be properly identified by the method of the present disclosure.

The term "cardiac intervention" encompasses those treatment regimens considered appropriate by the person skilled in the art. The term comprises interventions by surgery, microsurgery, and other invasive therapies affecting the cardiovascular system such as, the heart, as well as conservative (non-surgery) methods of treatment. Conservative methods are known in the art and include non-pharmacological methods and pharmacological methods. Pharmacological methods relate to the administration of pharmaceuticals. Appropriate pharmaceuticals include ACE inhibitors, such as Enalapril, Captopril, Ramipril, Trandolapril; angiotensin receptor antagonists and aldosterone antagonists, such as Losartan, Valsartan, Irbesartan, Candesartan, Telmisartan, Eprosartan, Spironolactone; statines, in particular Atorvastatin, Fluvastatin, Lovastatin, Pravastatin, Rosuvastatin, Simvastatin; beta blockers like propenolol, metoprolol, bisoprolol, carvedilol, bucindolol, nebivolol; nitrates; adrenergic agonists, like dobutamine, dopamine, epinephrine, isoprotenerol, norepinephrine, phenylephrine; antiplatelet agents, such as aspirin and clopidrogel; anticoagulants, such as warfarin, heparin, thrombin inhibitors, thrombinolytic drugs. Cardiac interventions as used herein may be treatment regimens which aim to restore the proper oxygen supply of the heart. This may be achieved by restoring the blood flow throughout the blood vessels supporting the heart, i.e. the coronary blood vessels. Those blood vessels may be impaired due to, e.g., thrombotic or atherosclerotic plaques. Accordingly, cardiac interventions may comprise a destruction and/or removal of such plaques and a restoration of the vessel, if necessary. Some cardiac interventions in accordance with the present disclosure are selected from the group consisting of percutaneous coronary angioplasty, percutaneous transluminal coronary balloon angioplasty, laser angioplasty, coronary stent implantation, bypass implantation or intraluminal techniques aiming to restore blood flow, vessel patency, stabilize plaque, and/or reduce intracoronary thrombus load.

In case an individual suffers from a circulatory impairment (as indicated by elevated levels of an ANP type natriuretic peptide), the circulatory impairment in general resolves when the cause underlying ischemia is remedied.

Further embodiments relate to the diagnosis of myocardial infarction in a subject. This method for diagnosing myocardial infarction in a subject comprises at least one of the following steps:
a) determining the amounts of a natriuretic peptide and/or troponin T in a sample of the subject;
b) comparing the amounts determined in step a) with reference amounts; and
c) diagnosing myocardial infarction, preferably based on the results obtained in step
d) preferably based on the results obtained in steps a) and b).

The person skilled in the art is aware that the concentrations cited in the present application for the cardiac troponins (troponin T or a variant thereof and troponin I or a variant thereof), NT-proANP or a variant thereof and—to a lesser extent—for sFLT-1 or a variant thereof, HGF or a variant thereof, H-FABP or a variant thereof and myoglobin or a variant thereof may not apply for patients suffering from impaired renal function, patients suffering from renal failure, and/or patients suffering from chronic and end stage renal failure. In an exemplary embodiment of the present disclosure, patients suffering from impaired renal function, renal failure, and/or chronic and end stage renal failure are not comprised in (excluded from) the methods of the present disclosure. In other embodiments, patients with renal hypertension are not comprised in (excluded from) the methods of the present disclosure. As used herein, "renal failure" is regarded as an impaired glomerular filtration rate (GFR) lying below the usual ranges of 60 to 120 ml/min, and in some cases below 60 ml/min. Chronic renal failure is a long-standing, progressive deterioration of renal function which often results in end stage renal failure. End stage renal failure is diagnosed when the GFR reaches a rate of up to about 30 ml/min. GFR is determined by the creatinine clearance, which is known to the person skilled in the art. Subjects with impaired renal function show higher levels of troponin I and troponin T than those cited above, due to an impaired clearance of the peptide. The levels vary with the severity of the renal impairment.

The severity of renal impairment may be divided into various grades, as displayed below (Source: National Kidney Foundation, as published in: Am J. Kidney Dis 39 suppl 1, 2002; Clinical Practice Guidelines for chronic kidney disease):
0: ≥90 ml/min
1: ≥90 ml/min with microalbuminuria
2: ≥60-<90 ml/min
3: ≥30-<60 ml/min
4: ≥15-<30 ml/min
5: <15 ml/min Moreover, encompassed by the present disclosure is a kit or device for carrying out the methods of the present disclosure comprising means for determining the amount of sFLT-1 and, optionally, HGF in a sample of a subject and means for comparing said amount to at least one reference amount.

The term "kit" as used herein refers to a collection of the aforementioned means, for example, provided separately or within a single container. The kit may in addition comprise means for determining the amount of a cardiac Troponin. Optionally, the kit may additionally comprise a user's manual for interpreting the results of any measurement(s) with respect to diagnosing the ischemic state in a subject as defined in the present disclosure. Particularly, such manual may include information about what determined amounts corresponds to what kind of diagnosis. This is outlined in detail elsewhere in this specification. Additionally, such user's manual may provide instructions about correctly using the components of the kit for determining the amount of the respective biomarkers.

The term "device" as used herein relates to a system of means comprising at least the aforementioned means operatively linked to each other as to allow the diagnosis of the ischemic state or the identification of a subject being susceptible to cardiac intervention. The device disclosure may in addition comprise means for determining the amount of a cardiac Troponin. Exemplary means for determining the amount of sFLT-1 and HGF and means for carrying out the comparison are disclosed above in connection with the method of the disclosure. How to link the means in an operating manner will depend on the type of means included into the device. For example, where means for automatically determining the amount of the peptides are applied, the data obtained by said automatically operating means can be processed by, e.g., a computer program in order to obtain the desired results. The means may comprise a single device in such a case. Said device may accordingly include an analyzing unit for the measurement of the amount of the peptides or polypeptides in an applied sample and a computer unit for processing the resulting data for the evaluation. Alternatively, where means such as test stripes are used for determining the amount of the peptides or polypeptides, the means for comparison may comprise control stripes or tables allocating the determined amount to a reference amount. The test stripes may be coupled to a ligand which specifically binds to the peptides or polypeptides referred to herein. The strip or device may comprise means for detection of the binding of said peptides or polypeptides to the said ligand. Exemplary means for detection are disclosed in connection with embodiments relating to the method of the disclosure above. In such a case, the means are operatively linked in that the user of the system brings together the result of the determination of the amount and the diagnostic or prognostic value thereof due to the instructions and interpretations given in a manual. The means may appear as separate devices in such an embodiment and may be packaged together as a kit. The person skilled in the art will realize how to link the means without further ado. Exemplary devices are those which can be applied without the particular knowledge of a specialized clinician, e.g., test stripes or electronic devices which merely require loading with a sample. The results may be given as output of raw data which need interpretation by the clinician. The output of the device is, however, processed, i.e. evaluated, raw data the interpretation of which does not require a clinician. Further, devices according to the present disclosure comprise the analyzing units/devices (e.g., biosensors, arrays, solid supports coupled to ligands specifically recognizing the sFLT-1 or HGF, Plasmon surface resonance devices, NMR spectrometers, mass-spectrometers etc.) or evaluation units/devices referred to above in accordance with the method of the disclosure.

The present disclosure also relates to the use of a kit or device for determining the amount of sFLT-1 and, optionally, HGF in a sample of a subject of sFLT-1 and, optionally, HGF and/or means for determining the amount of sFLT-1 and, optionally, HGF and/or means for comparing the amount of sFLT-1 and, optionally, HGF to at least one reference amount for: diagnosing the ischemic state in a subject showing the signs and symptoms of acute coronary syndrome but not fulfilling the diagnostic criteria for a myocardial infarction; and/or monitoring the severity of the ischemic state in the said subject; and/or stratifying/assessing the risk of the said subject to suffer from a myocardial infarction; and/or identifying a said subject which is susceptible to cardiac intervention; and/or deciding on the possible cardiac intervention of a said subject.

The present disclosure also relates to the use of at least one antibody against sFLT-1 and, optionally, HGF and/or means for determining the amount of sFLT-1 and, optionally, HGF and/or means for comparing the amount of sFLT-1 and, optionally, HGF to at least one reference amount for the manufacture of a diagnostic composition for: diagnosing the ischemic state in a subject showing the signs and symptoms of acute coronary syndrome but not fulfilling the diagnostic criteria for a myocardial infarction; and/or monitoring the severity of the ischemic state in the said subject; and/or stratifying/assessing the risk of the said subject to suffer from a myocardial infarction; and/or identifying a said subject which is susceptible to cardiac intervention; and/or deciding on the possible cardiac intervention of a said subject.

All references cited in this specification are herewith incorporated by reference with respect to their entire disclosure content and the disclosure content specifically mentioned in this specification.

The following examples are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

In the following examples, the following tests were used for the determination of the amounts of the respective peptides:

Troponin T was determined with the high sensitive hs Troponin T immunoassay test by Roche Diagnostics, using the ELECSYS 2010 Analyser. 1st incubation: 50 µL of sample, a biotinylated monoclonal anti-cardiac troponin T-specific antibody, and a monoclonal anti-cardiac troponin T-specific antibody labeled with a ruthenium complex (Ru (bpy)$^{2+}_3$) react to form a sandwich complex. 2nd incubation: After addition of streptavidin-coated microparticles, the complex becomes bound to the solid phase via interaction of biotin and streptavidin. The reaction mixture is aspirated into the measuring cell where the microparticles are magnetically captured onto the surface of the electrode. Unbound substances are then removed. Chemiluminescent emission is induced by application of a voltage to the electrode and is measured by a photomultiplier. Results are determined via a calibration curve.

HGF (hepatocyte growth factor) was tested by enzyme linked immunoassay (RD Systems, Minneapolis, Catalogue Nr. DHG00) using a monoclonal antibody specific for HGF and a precoated microplate. Standards and samples are pipetted into the wells and any HGF present is bound by the immobilized antibody. After washing away unbound substances, an enzyme-linked polyclonal antibody specific for HGF is added to the wells. Following a wash to remove any unbound antibody-enzyme reagent, a substrate solution is added to the wells and colour develops in proportion to the amount of HGF bound in the initial step. The colour development is stopped and the intensity of the colour is measured NT-proANP was determined with the proANP ELISA assay (B1-20892) obtained from Biomedica, Vienna, Austria. This sandwich assay comprises a polyclonal sheep NT-proANP specific antibody bound to a microtiterstrip. The sample is added to the microtiterstrip so that the proANP can bind to the antibody. After binding of the proANP to the first antibody a second proANP specific antibody is added to the vessel. This second antibody is conjugated with horseradish peroxidase (HRP). After incubation the unbound enzyme-conjugated antibody is removed by washing the microtiterstrip. Finally, tetramethylbenzidine (TMB) is added as a substrate for the HRP. The more proANP the sample contains, the more conjugated antibody binds. Thus, the total activity of HRP present in the vessel depends on the amount of proANP in the sample and the initial rate of TMB converted is a measure for the amount of NT-proANP in the sample.

sFlt-1 was determined with a sFlt-1 immunoassay to be used with the Elecsys and COBAS analyzers from Roche Diagnostics, Mannheim, Germany. The assay is based on the sandwich principle and comprises two monoclonal sFlt-1 specie antibodies. The first of these is biotinylated and the second one is labeled with a Tris(2,2'-hipyridyl)ruthenium (TT)-complex. In a first incubation step both antibodies are incubated with the sample. A sandwich complex comprising sFlt-1 and the two different antibodies is formed. In a next incubation step streptavidin-coated beads are added to this complex. The beads bind to the sandwich complexes. The reaction mixture is then aspirated into a measuring cell where the beads are magnetically captured on the surface of an electrode. The application of a voltage then induces a chemiluminescent emission from the ruthenium complex which is measured by a photomultiplier. The amount of light is dependent on the amount of sandwich complexes on the electrode.

The named tests are also preferably employed in the general context of the present disclosure for the determination of the respective peptides.

Example 1

Determination of Reference Values

149 Persons, mean age 42.8 years were tested for the presence of sFIT1, pro ANP and HGF, at the time of testing and within the previous 2 weeks they were asymptomatic, specifically they had no chest pain, there was also no evidence of cardiac dysfunction as indicated by NT-pro BNP testing.

Results (see Table 1):

TABLE 1

|  | NT-pro ANP | sFIT1 | HGF |
|---|---|---|---|
| Median | 780 pg/ml | 52 pg/ml | 0.16 pg/ml |
| 25% | 610 pg/ml | 42 pg/ml | 0.03 pg/ml |
| 75% | 850 pg/ml | 71 pg/ml | 0.35 pg/ml |
| 95% | 1320 pg/ml | 92 pg/ml | 0.62 pg/ml |
| 99% | 1674 pg/ml | 109 pg/ml | 0.73 pg/ml |

In the context of the present disclosure, the $95^{th}$ percentile may be regarded as an appropriate reference value: Individuals showing marker values above those are considered to suffer from an ischemic state. The $99^{th}$ percentile may define the reference value indicative for an ischemic state. In respect to NT-proANP, the $95^{th}$ and in some cases the $99^{th}$ percentile may be considered to be the reference value which defines which values are indicative of a circulatory impairment.

Example 2 sFIT-1, HGF and NT-proANP in Patients with Chest Pain and Suspected Acute Coronary Syndrome A total of 33 patients (mean age 62, 47-72), 21 males, 12 females who presented with signs and symptoms of acute coronary syndrome in the emergency room within 2 hours after the onset of symptoms were included into the study. 14/33 had a family history of chronic artery disease and 21/33 had an established coronary artery disease, 5/33 reported a previous myocardial infarction. All patients had normal kidney function as determined by serum creatinine, H-FABP and myoglobin were below the cutoff value for future myocardial infarct (MI) (see WO 2008/145689, WO 2009/033831). Patients included into the analysis were patients which did not meet the criteria of NON-STEMI at the end of follow up. All patients met the criteria of the Joint ESC/ACCF/AHA/WHF Task Force for the Redefinition of Myocardial Infarction (The Joint European Society of Cardiology/American College of Cardiology Committee: Universal definition of myocardial infarction, European Heart Journal (2007) l.c.), in that in all samples measured the troponin amount was below the 99 percentile (0.14 ng/ml, mean 0.079 ng/ml) at all timepoints measured and during the recommended time interval (at presentation and (at least) 6-9 hours after presentation).

All patients had no increase in myoglobin, H-FABP or NT-pro BNP (plus/minus 20%) during the course of the observation period. Thus, in none of the patients selected for the present study showed a myocardial infarction according to current guidelines. Changes in the level of sFIT1/HGF were observed in 27 patients and no changes occurred in 6 patients, indicating that 27 patients had biochemical evidence of ischemia and 6 patients lacked such signs. Acute changes in circulatory function were observed in 11 patients as indicated in changes in NT-proANP concentrations. Acute changes in circulatory function were only observed in patients with laboratory evidence of ischemia.

Serum samples were drawn by venipuncture, centrifuged within 30 minutes and the serum supernatant was kept at −20 C until analysed.

Tests were performed according to the instructions of the manufacturer.

Table 2 illustrates observed changes in sFIT1 and/or HGF in 33 patients presenting with acute coronary syndrome and without development of myocardial infarction.

Table 3 feature individual results of selected patients.

Patient No. 14 presented with biochemical evidence of ischemia as indicated by increased concentration of HGF and sFIT1. In the course of the observation, sFIT1 and HGF levels declined indicating reversal of biochemical evidence of ischemia which was compatible of pain relief in this patient without further medication (patient received nitroglycerin spray by emergency physician before presentation to the emergency room). Pro ANP levels slightly increased during the observation period indicating no significant acute functional changes caused by the event.

Patient No. 21 presented with signs and symptoms of ACS that returned for approximately 5 minutes during the visit in the emergency room, sFIT1 was slightly elevated at presentation, then decreased and again increased which was compatible with the observed chest pain during the observation period. Initial chest pain was associated with significant functional changes as indicated by a significant increase in pro ANP levels shortly after presentation. This was compatible to an observed ventricular tachycardia (for approximately 30 seconds) in the ambulance during transport to the emergency room.

Patient No. 40 presented with a severe episode of ischemia as confirmed by increased and increasing sFIT1 and HGF levels relative to the above defined reference amounts, the patients also showed evidence of acute functional changes as indicated by a significant increase in pro ANP levels one hour after presentation to the emergency room. Using nitroglycerin spray symptoms of ischemia disappeared, so did biochemical evidence of ischemia, the patients did not develop myocardial infarction.

Patient No. 42 was admitted with signs and symptoms of ACS, at presentation significantly elevated sFIT1 and HGF levels were observed when compared to the above defined reference amounts. During follow up sFIT1 and HGF declined slowly indicating initial severe ischemia followed by moderate ischemia with finally resolved. Slight increases of pro ANP were observed at presentation and at 24 h follow up.

Patient No. 43 presented with signs and symptoms of ACS, that were no longer present at presentation to the emergency room. He had slightly elevated sFIT1 and HGF levels relative to the above defined reference amounts but no definite biochemical signs of ischemia. His pro ANP levels did not change during the total observation period. Based on the clinical presentation he was finally considered to suffer from non-cardiac symptoms while a coronary artery disease was known to be present in this patient.

Patient No. 52 presented with ACS still present at presentation to the emergency room. He was treated with nitroglycerin spray and symptoms disappeared. During ECG monitoring in the emergency room significant arrhythmia was not recognized. Biochemical evidence of ischemia was reversible as evidenced by sFIT1 and HGF measurement (marker levels increased or decreased, depending on the degree of ischemia. Slight changes in pro ANP levels were observed during presentation to the emergency room.

TABLE 2

The patients did not develop myocardial infarction.

| Patient No. | Time Interval Hours After hospital presentation | TnT ng/ml | HGF pg/ml | sFlt-1/pg/ml | NTpro-ANP/pg/ml |
|---|---|---|---|---|---|
| 14 | 0 | 0.0052 | 37.44 | 6631.95 | 4115.65 |
|  | 1 | 0.0059 | 11.49 | 1668.09 | 4500.56 |
|  | 2 | 0.0061 | 7.11 | 680.64 | 5151.40 |
|  | 3 | 0.0058 | 7.93 | 717.12 | 5900.91 |
| 21 | 0 | 0.0049 | 1.89 | 431.66 | <635 |
|  | 1 | 0.0058 | 0.88 | 83.96 | 36963.76 |
|  | 2 | 0.0042 | 0.70 | 431.00 | 45324.67 |
|  | 3 | 0.0061 | 1.01 | 71.90 | 31076.23 |
|  | 4 | 0.0057 | 1.16 | 17.10 | 25059.18 |
| 40 | 2 | 0.0112 | 55.34 | 359.75 | <635 |
|  | 3 | 0.0109 |  | 6425.50 | 6463.30 |
|  | 4 | 0.0118 | 35.87 | 4315.16 | 6168.70 |
|  | 5 | 0.0121 | 23.94 | 2715.41 | 5628.02 |
|  | <24 h pl | 0.0109 | 0.77 | 182.78 | 7271.33 |
| 42 | 0 | 0.0121 | 21.50 | 9041.81 | 23094.70 |
|  | 1 | 0.0139 | 11.96 | 4677.82 | 18533.80 |
|  | 2 | 0.0132 | 8.69 | 1561.08 | 15476.21 |
|  | 3 | 0.0119 | 7.04 | 1150.10 | 16769.73 |
|  | 4 | 0.0108 | 8.36 | 1203.32 | 17845.08 |
|  | 5 | 0.0112 | 8.45 | 1083.85 | 16433.54 |
|  | 6 | 0.0098 | 7.87 | 1070.64 | 16842.25 |
|  | <24 h pl | 0.0101 | 1.31 | 176.77 | 25900.17 |
| 43 | 0 | 0.0046 | 0.80 | 128.98 | 16689.61 |
|  | 2 | 0.0042 | 0.63 | 117.12 | 15619.63 |
|  | 3 | 0.0039 | 0.67 | 117.12 | 19013.81 |
|  | 4 | 0.0041 | 0.65 | 117.12 | 18435.65 |
| 52 | 0 | 0.0098 | 17.08 | 45.02 | 15668.18 |
|  | 2 | 0.0106 | 16.42 | 2329.96 | 24974.49 |
|  | 3 | 0.0111 | 9.06 | 1315.80 | 21617.98 |
|  | 4 | 0.0131 | 7.28 | 941.52 | 19231.37 |
|  | 5 | 0.0129 | 7.05 | 816.68 | 15239.65 |

TABLE 3

Number of patients displaying changes in sFlt-1 and/or NT-proANP of at least 20% from baseline values

|  | sFLT-1 change | NT-proANP change |
|---|---|---|
| yes | 27 | 6 |
| no | 6 | 0 |

Comparative Example 1 sFIT-1, HGF and NT-proANP in Patients with MI 22 patients who developed myocardial infarction had troponin T concentrations that did not meet the criteria of the Joint ESC/ACCF/AHA/WHF Task Force for the Redefinition of Myocardial Infarction (The Joint European Society of Cardiology/American College of Cardiology Committee: Universal definition of myocardial infarction, European Heart Journal (2007) l.c., although 4 patients (including Patient 2, Table 4) had a troponin T concentration above the 99% percentile of a normal reference population. The reference population developing MI simply illustrates that all patients developing MI had increased sFIT1 and HGF in comparison to the healthy reference population as outlined in Table 1. (and thereby serves as a "positive control") in this study.

In all patients sFIT1, HGF and pro ANP were increased at entry into the study when compared to the above defined reference amounts two such patients are demonstrated in Table 4. 6 Patients were diagnosed with STEMI (i.e. they met the criteria of NON-STEMI according to the Joint ESC/ACCF/AHA/WHF Task Force for the Redefinition of Myocardial Infarction (The Joint European Society of Cardiology/American College of Cardiology Committee: Universal definition of myocardial infarction, European Heart Journal (2007) l.c.) at the end of follow up). All other patients had NON-STEMI according to the Joint ESC/ACCF/AHA/WHF Task Force for the Redefinition of Myocardial Infarction.

Patient No. 1: presented with the signs and symptoms of ACS, at presentation he had elevated sFIT1 and HGF levels relative to the above defined reference amounts that declined during follow up and after signs of ischemia resolved. At 4 h after hospital presentation Troponin T levels increased, so did NT-proANP as a sign of acute functional change. Because of increasing Troponin T levels he was subjected to coronary angiography and the patient had a STENT implanted.

Patient No. 2: presented with signs and symptoms of ACS that were still present at presentation to the emergency room. On ECG he had ST-elevation in II, III and aVF, indicating a myocardial infarction of the posterior wall of the left ventricle. He had highly elevated sFIT1 and HGF levels relative to the above defined reference amounts, Troponin T was increased when compared to the above defined reference amount but not diagnostic for non-STEMI at this time. He was immediately scheduled for angiography, just before intervention a second sample was obtained showing an increase in NT-proANP and Troponin T and continuously elevated levels of HGF and sFIT1 relative to the above defined reference amounts. At angiography a STENT was implanted and coronary flow was re-established.

The results are shown in the following table 4

TABLE 4 sFIT-1, HGF and NT-proANP in patients with MI

| Patient No. | Diagnose | Time Interval/hours after hospital presentation | TnT hs pg/ml | NTproANP pg/ml | HGF ng/ml | sFlt-1 pg/ml |
|---|---|---|---|---|---|---|
| 1 | NonSTEMI | 0 | 1.81 | 4611.05 | 7.21 | 2160.48 |
|  | NonSTEMI | 4 hours | 20.33 | 6431.66 | 1.51 | 274.03 |
| 2 | STEMI | 0 | 22.03 | 13826.19 | 62.64 | 7382.76 |
|  | STEMI | 2.5 hours | 481.41 | 27423.76 | 57.25 | 6673.91 |

The data show that the amounts of sFLT-1 and HGF are more elevated in more severe ischemia (STEMI vs. NSTEMI). sFLT-1 and HGF give short-term information on the ischemic state, as can be seen by the fact that their respective amounts decrease even in STEMI patients after several hours. The data show, furthermore, that ischemia may cause a circulatory dysfunction, as indicated by the elevated NT-proANP levels.

All publications, patents and applications are hereby incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for diagnosing an ischemic state in myocardium of a subject showing signs and symptoms of acute coronary syndrome but not fulfilling the diagnostic criteria for a myocardial infarction of an amount of troponin T determined in a sample of the subject greater than 0.1 ng/ml, comprising:
   contacting a portion of a sample from a subject with an antibody having specific binding affinity for soluble fms-like tyrosine kinase-1 (sFLT-1), thereby forming a complex between the antibody and sFLT-1, the antibody having a detectable label;
   separating the complex formed in said step of contacting from antibody not comprising the complex;
   quantifying a signal from the detectable label of the antibody comprising the complex formed in said step of contacting, the signal being proportional to an amount of sFLT-1 in the sample, whereby an amount of sFLT-1 in the sample is calculated;
   comparing the amount of sFLT-1 determined in said step of quantifying to a sFLT-1 reference amount; and
   providing a diagnosis of an ischemic state in myocardium of the subject if the amount of sFLT-1 in the sample calculated in said step of quantifying is greater than the sFLT-1 reference amount.

2. The method of claim 1, wherein the sFLT-1 reference amount is about 92 pg/ml.

3. The method of claim 2, wherein said step of providing a diagnosis further comprises providing a diagnosis of an ischemic state associated with cardiac dysfunction.

4. The method of claim 1 further comprising the steps of:
   determining an amount of one of hepatocyte growth factor (HGF) or a variant thereof; and
   comparing the amount of the one of the hepatocyte growth factor and the variant thereof to a HGF reference value, wherein said step of providing is further based on said step of comparing the amount of the one of the hepatocyte growth factor and the variant thereof to the HGF reference value.

5. The method of claim 4, wherein the sFLT-1 reference amount is about 92 pg/ml and the HGF reference value is about 0.62 pg/ml, said step of providing a diagnosis comprising providing a diagnosis of an ischemic state associated with cardiac dysfunction if the amount of sFLT-1 is greater than the sFLT-1 reference amount and the amount of the one of HGF and the variant thereof is greater than the HGF reference value.

6. The method of claim 1 further comprising the step of determining an amount of one of an ANP-type peptide and a variant thereof in the sample of the subject wherein said step of providing a diagnosis further comprises providing a diagnosis of a circulatory impairment if the amount of the one of the ANP-type peptide and variant thereof is at least equal to about 1320 pg/ml.

7. The method of claim 6, wherein the ANP-type peptide is NT-proANP.

8. The method of claim 1 further comprising at least one of the steps of determining an amount of myoglobin or a variant thereof, and determining an amount of a heart fatty acid binding protein (HFABP) or a variant thereof of in the sample.

9. The method of claim 1, wherein said step of providing a diagnosis is performed by a computing device.

10. The method of claim 1 further comprising the step of recommending a cardiac intervention if an ischemic state is diagnosed, wherein the cardiac intervention is selected from the group consisting of: administration of a pharmaceutical; percutaneous coronary angioplasty; percutaneous transluminal coronary balloon angioplasty; laser angioplasty; coronary stent implantation; bypass implantation; and an intraluminal technique aiming to restore one of blood flow, vessel patency, stabilize plaque, and reduction of intracoronary thrombus load.

11. The method of claim 1, wherein the subject showing signs and symptoms of acute coronary syndrome but not fulfilling the diagnostic criteria for a myocardial infarction of an amount of troponin T determined in a sample of the subject greater than 0.1 ng/ml also has an electrocardiogram non-diagnostic for myocardial infarction.

12. A method for diagnosing a subject presenting with symptoms of acute coronary syndrome, but not fulfilling the diagnostic criteria for a myocardial infarction of an amount of troponin T determined in a sample of the subject greater than 0.1 ng/ml and having an electrocardiogram non-diagnostic for myocardial infarction, as in need of cardiac intervention therapy, comprising:
   contacting a portion of a sample from a subject obtained at a first point in time with an antibody having specific binding affinity for soluble fms-like tyrosine kinase-1 (sFLT-1), thereby forming a complex between the antibody and sFLT-1, the antibody having a detectable label;
   separating the complex formed in said step of contacting from antibody not comprising the complex;
   quantifying a signal from the detectable label of the antibody comprising the complex formed in said step of contact, the signal being proportional to an amount of sFLT-1 in the sample, whereby an amount of sFLT-1 in the sample is calculated;
   contacting a portion of a second sample from the subject, obtained at a second point in time later than the first point in time, with an antibody having specific binding affinity for soluble fms-like tyrosine kinase-1 (sFLT-1), thereby forming a complex between the antibody and sFLT-1, the antibody having a detectable label;
   separating the complex formed in said step of contacting from antibody not comprising the complex;
   quantifying a signal from the detectable label of the antibody comprising the complex formed in said step of contacting, the signal being proportional to an amount of sFLT-1 in the second sample, whereby an amount of sFLT-1 in the second sample is calculated;
   comparing the amount of sFLT-1 determined in the sample obtained at the first point in time to the amount of sFLT-1 determined in the second sample obtained at the second point in time; and providing a diagnosis of the subject being in need of cardiac intervention therapy if the amount of sFLT-1 in the second sample is greater than the amount of sFLT-1 in the sample obtained at the first point in time.

13. The method of claim 12, wherein said step of providing a diagnosis also comprises the amount of sFLT-1 in the second sample being greater than a reference amount of sFLT-1.

14. The method of claim 13, wherein the reference amount of sFLT-1 is about 92 pg/ml.

* * * * *